United States Patent [19]
Saito et al.

[11] Patent Number: 6,114,364
[45] Date of Patent: Sep. 5, 2000

[54] 2,3-DISUBSTITUTED CYCLOPENTANONE DERIVATIVES, PROCESS FOR PRODUCING THE SAME, AND MEDICINAL USE THEREOF

[75] Inventors: Seiichi Saito, Chiba; Tomio Morino; Kuniko Masuda, both of Saitama, all of Japan

[73] Assignee: Nippon Kayaku Co., Ltd., Tokyo, Japan

[21] Appl. No.: 09/117,411

[22] PCT Filed: Jan. 31, 1997

[86] PCT No.: PCT/JP97/00247

§ 371 Date: Oct. 5, 1998

§ 102(e) Date: Oct. 5, 1998

[87] PCT Pub. No.: WO97/28114

PCT Pub. Date: Aug. 7, 1997

[30] Foreign Application Priority Data

Jan. 31, 1996 [JP] Japan ................................ 8-035834
Oct. 16, 1996 [JP] Japan ................................ 8-293184

[51] Int. Cl.[7] .......................... A61K 31/44; C07D 213/60
[52] U.S. Cl. .......................... 514/350; 546/301; 546/290; 514/256; 514/345; 514/423; 514/463; 514/530; 514/546; 544/335; 548/530; 549/453; 560/121; 560/126; 560/129; 560/231; 562/503; 562/553
[58] Field of Search .................................. 514/256, 345, 514/423, 463, 530, 546, 557, 350; 546/290, 301; 548/530; 549/453; 562/503, 553, 577; 560/121, 129, 231, 126; 544/335

[56] References Cited

U.S. PATENT DOCUMENTS 5,505,944  4/1996  Morino et al. ........................ 424/117
5,804,186  9/1998  Komagata et al. ................... 424/117

FOREIGN PATENT DOCUMENTS 0 760 242   3/1997   European Pat. Off. .
50-101337   8/1975   Japan .
55-124738   9/1980   Japan .
7/31992    11/1995   Japan .
08231469    9/1996   Japan .

OTHER PUBLICATIONS

Tetrahedron Letters; vol. 35, No. 22 (1994); pp. 3755–3758; Nangia, A. et al.
Tetrahedron Letters; vol. 45, No. 22, (1989); pp. 7023–7030; Mikolajczyk, Marian et al.
Tetrahedron Letters; vol. 28, No. 19 (1987); pp. 2147–2150; Otera, Junzo et al.
Tetrahedron Letters; vol. 43, No. 2; (1987); pp. 317–322; Froissant, Jacques et al.
J. Org. Chem. (1980), 45(4), p. 752–754; Boeckman, Robert K. et al.
J. Org. Chem (1992), 57(18), p. 4895–4903; Tamura, Rui et al.
Tetrahedron Lett. (1989), 30 (52), p. 7381–7382; Amri, Hassen et al.
Tetrahedron Lett. (1987), 28 (43), p. 5083–5086; Matlin, Albert R. et al.
J. Org. Chem. (1985), 50(16), p. 2965–2968; Cohen, Theodore et al.
J. Org. Chem. (1982), 47(17), p. 3306–3310; Marx, John N. et al.
Copy of the International Search Report dated May 20, 1997.

*Primary Examiner*—Alan L. Rotman
*Assistant Examiner*—Charanjit S. Aulakh
*Attorney, Agent, or Firm*—Nields, Lemack & Dingman

[57] ABSTRACT

The present invention relates to a compound represented by the following general formula (1)

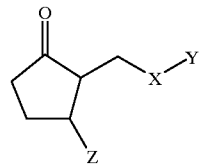

(wherein X represents O, S, SO, SO$_2$, or NH, Y is a substituted or unsubstituted hydrocarbon residue containing 1 through 6 carbon atoms and having an overall molecular weight of not less than 15 and not more than 400, and the hydrocarbon residue, when the residue is ring, may contain one or two hetero-atoms in the ring, and Z is a carboxyl group, a group derived therefrom or an aliphatic hydrocarbon residue having from 1 to 4 carbon atoms which may be substituted or unsabstituted) or a pharmacologically acceptable salt thereof (excluding (1R,2S)-2-[(2R)-(2-acetyl-amino-2-carboxyethyl)thiomethyl]-3-oxo-1-cyclopentane-carboxylic acid (cystacyclin)), a method for production thereof and a medicinal use thereof. The compound of the present invention is useful as a neuron differentiation accelerator.

15 Claims, No Drawings

2,3-DISUBSTITUTED CYCLOPENTANONE DERIVATIVES, PROCESS FOR PRODUCING THE SAME, AND MEDICINAL USE THEREOF

This application is a §317 of PCT/JP97/00247 filed on Jan. 31, 1997, now WO97/28114 published Aug. 7, 1997.

TECHNICAL FIELD

This invention relates to 2,3-di-substituted cyclopentanone derivatives, process for producing the same, and medicinal use thereof, especially new neuron differentiation accelerator.

BACKGROUND ART

It is demonstrated that the nerve growth factor (hereinafter referred to as "NGF") shows, in vitro, manifesting a regenerative activity on nerve cells of senile animals because NGF has an activity for elongating neurite and regulating aproduction of aneurotransmitter [("Age," Vol. 8, page 19 (1985)]. On the other hand, it is known that the PC 12 cells which are the cells of the strain produced by cloning a species of brown cells of murine adrenal medulla, are caused by addition of NGF to cease propagation and succumb to differentiation into sympathetic nerve-like cells having neurite. Since the NGF has these activities, this has been drawn attention as an antidemential pharmaceutical compositions in recent years. It has been studied that fibroblast growth factor or Interleukin 6 etc. besides NGF induces the growth of neurite by using these cell. Further also, recently, it has shown that SUTAROSUPORIN of a low molecular substance likewise induce elongation of neurite ["Neurochemistry," Vol. 26, pp. 200–220 (1987)].

Since SUTAROSUPORIN mentioned above is a low molecular substance, which differs from NGF, the development for medical use is expected. However, this is not utilized at the present time because of a strong toxicity.

Recently, the physiologically active substance NK 175203 produced by the microorganism of Streptomyces sp. NK 175203 (FERM BP-4372) has been found to have an activity for inducing elongation of neurite (WO 95/31992).

The physiologically active substance NK 175203 (hereinafter referred to as "cystacyclin") is expected to develop into medicine because it is a low molecular compound manifesting low toxicity. But the product amount is only a little because it is produced by the microorganism. Thus, there has been demanded for supply of a low molecular compound obtained by chemical synthesis, which has low toxicity and has a strong activity for promoting induction of neurite.

DISCLOSURE OF THE INVENTION

As the results of the various studies for the structure analysis of cystacyclin and the derivatives thereof, the present inventors have found that cyclopentanone derivative needs at least one substituted lower alkyl group as a substituent on the ring of cyclopentanone in order to having the activity for promoting nerve differentiation. The preferable compound in the activity is a cyclopentanone derivative having one substituted lower alkyl group on the ring of cyclopentanone and an another substituent in the next position. The present inventors have found that the more preferable compounds are 2,3-di-substituted cyclopentanone derivatives shown as the general formula (I) described below or the pharmacologically acceptable salt thereof and completed the present invention.

The present invention relates to a 2-substituted lower alkyl-3-substituted cyclopentanone derivative or the pharmacologically acceptable salt thereof, and the process for the production thereof and a pharmaceutical composition comprising it.

In more detail, the present invention relates to 2,3-di-substituted cyclopentanone derivative represented by the following the general formula (I)

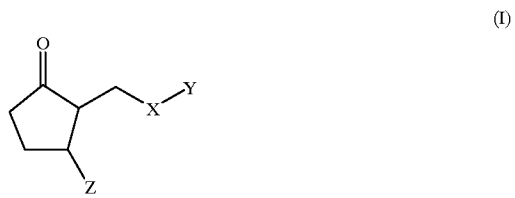

wherein X is O, S, SO, $SO_2$, or NH;
Y is a hydrocarbon residue having 1–6 carbon atoms, which is substituted or unsubstituted, and having a whole molecular weight of from 15–400 in the residue, and may contain 1 or 2 hetero atoms in the ring when the hydrocarbon residue is a cyclic group, and
Z is carboxyl group, a group derived therefrom, an aliphatic hydrocarbon residue having 1–4 carbon atoms, which is substituted or unsubstituted,
or a pharmacologically acceptable salt thereof, and a process for production thereof, and a pharmaceutical composition comprising it.

The present invention provides a novel compound having an activity for accelerating differentiation of neurons. The compound of the present invention having two or more asymmetric carbon atoms therein may be an optically active substance or optically inactive substance and it is suitable that the present compound is an optically active substance.

Also, the present invention provides the pharmaceutical composition which comprises the said compound and is useful as the accelerator for differentiation of neurons.

The compound of the present invention has the activity for differentiation of neurons and is useful as the antidemential agent, the protector of neurons, the agent for curing peripheral neuropathy caused by diabetes and other disease, therefore, the present invention provides an agent and a method for the treatment of these disease.

Also, in detail, the present invention relates to the following inventions.

(1) The present invention relates to a pharmaceutical composition comprising a 2,3-di-substituted cyclopentanone derivative having an activity for accelerating differentiation of neurons and the following general formula (I)

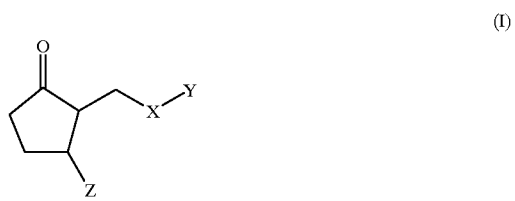

wherein X is O, S, SO, $SO_2$, or NH;
Y is a hydrocarbon residue having 1–6 carbon atoms, which is substituted or unsubstituted, and having the whole molecular weight of from 15–400 in the residue, and may contain 1 or 2 hetero atoms in the ring when the residue is a cyclic group; and Z is carboxyl group, a group derived therefrom or an aliphatic hydrocarbon residue having 1 to 4 carbon atoms which is substituted or unsubstituted, or a pharmacologically acceptable salt thereof, except for (1R, 2S)-2-[(2R)-(2-acetylamino-2-carboxy ethyl)thio methyl]-3-oxo-1-cyclopentanecarboxylic acid(cystacyclin), as an active component.

Furthermore, the present invention relates to the pharmaceutical composition comprising the active component and a pharmaceutically acceptable carrier.

(2) The present invention relates to a neuron differentiation accelerator comprising the 2,3-di-substituted cyclopentanone derivative (except cystacyclin) of the general formula (I) in (1) mentioned above or a phamacologically acceptable salt thereof as an active ingredient.

Furthermore, the present invention relates to the pharmaceutical composition useful as a neuron differentiation accelerator in (1) mentioned above.

(3) The present invention relates to the pharmaceutical composition or a neuron differentiation accelerator of (1) or (2) mentioned above, wherein the 2,3-di-substituted cyclopentanone derivative or a pharmacologically acceptable salt thereof is characterized by that the hydrocarbon residue having 1 to 6 carbon atoms of Y in the general formula (I) in (1) mentioned above is

[1] an alkyl group having 1–6 carbon atoms which is substituted by one to three substituents or

[2] pyridino group or pyrimidinyl group which may be substituted by one to three substituents, and each substituent is selected from the group consisting of (i) carboxyl group or a group derived therefrom, (ii) amino group or a group derived therefrom, and (iii) hydroxy group or a group derived therefrom.

(4) The present invention relates to the neuron differentiation accelerator comprising the 2,3-di-substituted cyclopentanone derivative or a pharmacologically acceptable salt thereof in (3) mentioned above as an active ingredient or the pharmaceutical composition further comprising a pharmaceutically acceptable carrier, wherein (A) the each substituent in Y of the general formula (I) in (1) mentioned above is (i) carboxyl group or a group derived therefrom, shown as —$COR_1$; $R_1$ is —$OR_2$ or —$NR_3R_4$; $R_2$ is H or hydrocarbon residue having 1–6 carbon atoms; $R_3$ and $R_4$ are H, alkyl group having 1–6 carbon atoms or acyl group having 1–20 carbon atoms which may have one or more substitents, respectively, (ii) amino group or a group derived therefrom, shown as —$NR_5R_6$; $R_6$ and $R_6$ are H, alkyl group having 1–6 carbon atoms or acyl group having 1–20 carbon atoms respectively, or (iii) hydroxy group or a group derived therefrom, shown as—$OR_7$; $R_7$ is H or, a hydrocarbon residue having 1–6 carbon atoms or an acyl group having 1–20 carbon atoms, wherein they may have one or more substituents; and (B) a carboxyl group or a group derived therefrom of Z in the general formula (I) in (1) mentioned above is the group shown as —CO $R_8$ or —$CH_2OR_9$; and $R_8$ is independently same as $R_1$; $R_9$ is H, an alkyl group having 1–6 carbon atoms or an acyl group having 1–20 carbon atoms.

(5) The present invention relates to the neuron differentiation accelerator comprising the 2,3-di-substituted cyclopentanone derivative or a pharmacologically acceptable salt thereof as an active ingredient or the pharmaceutical composition further comprising a pharmaceutically acceptable carrier, wherein, in the general formula (I) in (1) mentioned above , the hydrocarbon residue having 1–6 carbon atoms in Y is

[1] an alkyl group having 1–6 carbon atoms which is substituted or

[2] a pyridino group or pyrimidinyl group, which is substituted, and the substituent is at least one selected from a group consisting of (i) carboxyl group or an alkoxycarbonyl group having 1 to 6 carbon atoms, (ii) amino group or an acylamino group, and (iii) hydroxy group or an alkoxy group having 1 to 6 carbon atoms, and, when the number of the substituents selected from these one are two or more, those substituents may be same or different groups, and Z is carboxyl group, an alkoxylcarbonyl group having 1–6 carbon atoms, hydroxymethyl group or an acyloxymethyl group having 1–20 carbon atoms.

(6) The present invention relates to the neuron differentiation accelerator comprising the 2,3-di-substituted cyclopentanone derivative or a pharmacologically acceptable salt thereof as an active ingredient or the pharmaceutical composition further comprising a pharmaceutically acceptable carrier, wherein, in the general formula (I) in (1) mentioned above, X is S, O, SO or $SO_2$ and the hydrocarbon residue having 1–6 carbon atoms in Y is an alkyl group having 1–4 carbon atoms which have one or two substituents and the each substituent is selected from a group consisting of (i) a carboxyl group or an alkoxycarbonyl group, (ii) amino group or an acylamino group, and (iii) hydroxy group or an alkoxy group, and, when there are two substituents, those substituents may be same or different groups, and Z is a carboxyl group, an alkoxycarbonyl group, hydroxymethyl group or acyloxymethyl group.

(7) The present invention relates to the neuron differentiation accelerator comprising the 2,3-di-substituted cyclopentanone derivative or a pharmacologically acceptable salt thereof as an active ingredient or the pharmaceutical composition further comprising a pharmaceutically acceptable carrier in (5) mentioned above, wherein, in the general formula (I) in (1) mentioned above, X is S, O or SO and Y is 2-carboxy-2-amino (or acylamino)-ethyl group, 2-alkoxycarbonyl (or alkenyloxycarbonyl)-2-aminoethyl group, 2-alkoxycarbonyl (or alkenyloxycarbonyl)-2-acylaminoethyl group, 2,3-dihydroxypropyl group, 2-hydroxyethyl group, or 2-amino(or acylamino)ethyl group; and Z is hydroxymethyl group or an acyloxymethyl group.

(8) The present invention relates to the neuron differentiation accelerator comprising the 2,3-di-substituted cyclopentanone derivative (except for cystacyclin)or a pharmacologically acceptable salt thereof as an active ingredient or the pharmaceutical composition further comprising a pharmaceutically acceptable carrier, wherein, in the general formula (I) in (1) mentioned above, (I) the group shown as —$CH_2$—X—Y is —$CH_2$—S—$CH_2$—CH(OH)—$CH_2OH$ and Z is —$CH_2OCOCH_3$, (II) the group shown as —$CH_2$—X—Y is —$CH_2$—S—$CH_2$—CH(COOH)NHCOCH$_3$ and Z is —$CH_2OCOCH_3$, (III) the group shown as —$CH_2$—X—Y is —$CH_2$—S—$CH_2$—CH(COOH)NHCOCH$_3$ and Z is —$CH_2OH$, (IV) the group shown as —$CH_2$—X—Y is —$CH_2$—S—$CH_2$—$CH_2$—NHCOCH$_3$ and Z is —$CH_2OCOCH_3$, (V) the group shown as —$CH_2$—X—Y is —$CH_2$—S—$CH_2$—$CH_2$—OH and Z is —$CH_2OCOCH_3$, (VI) the group shown as —$CH_2$—X—Y is —$CH_2$—S—[3-(COOCH$_3$)-pyridino-2-yl] and Z is —$CH_2OH$, (VII) the group shown as —$CH_2$—X—Y is —$CH_2$—S—$CH_2$—CH(COOCH$_3$)NHCOCH$_3$ and Z is —COOH, (VIII) the group shown as —$CH_2$—X—Y is —$CH_2$—S—$CH_2$—CH(COOCH$_2$—CH=CH$_2$)NHCOCH$_3$ and Z is —COOH, (IX) the group shown as —$CH_2$—X—Y is —$CH_2$—S—$CH_2$—CH(COOH)NHCOCH$_3$ and Z is —COOH, (X) the group shown as —$CH_2$—X—Y is —$CH_2$—S—$CH_2$—CH(COOH)NHCOCH$_3$ and Z is —COOCH$_3$, (XI) the group shown as —$CH_2$—X—Y is —$CH_2$—S—$CH_2$—$CH_2$—NHCOCH$_3$ and Z is —COOCH$_3$, (XII) the group shown as —$CH_2$—X—Y is —$CH_2$—S—$CH_2$—$CH_2$—NHCOCH$_3$ and Z is —COOH, or (XIII) the group shown as —$CH_2$—X—Y is —$CH_2$—O—$CH_2$—CH(OH)—$CH_2OH$ and Z is —$CH_2OH$, (9) The present invention relates to a 2,3-di-substituted cyclopentanone derivatives represented by the following general formula (I),

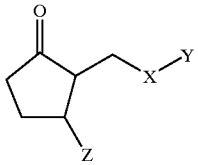

(I)

wherein X is O, S, SO, SO$_2$, or NH;

Y is a hydrocarbon residue having 1–6 carbon atoms, which is substituted or unsubstituted, and having a whole molecular weight of from 15–400 in the residue, and may contain 1 or 2 hetero atoms in the ring when the hydrocarbon residue is a cyclic group; and Z is carboxyl group, a group derived therefrom or an aliphatic hydrocarbon residue having 1 to 4 carbon atoms which is substituted or unsubstituted, or a pharmacologically acceptable salt thereof, except for that Z is unsubstituted hydrocarbon residue having 1–6 carbon atoms or aldehyde group when —X—Y is —S—Ph, that Z is —COOCH$_3$ or —CN when —X—Y is —SO—Ph or —SO$_2$—Ph, that Z is —COOCH$_3$ when —X—Y is —SO$_2$—CH$_3$, and that the compound represented by the general formula (I) is (1R, 2S)-2-[(2R)-(2-acetylamino-2-carboxy) ethylthio] methyl-3-oxo-1-cyclopentane-carboxylic acid (cystacyclin).

(10) The present invention relates to a 2,3-di-substituted cyclopentanone derivatives or a pharmacologically acceptable salt thereof wherein, in the general formula (I) in (1) mentioned above, X is a group shown as O, S, SO, or SO$_2$, and the hydrocarbon residue having 1–6 carbon atoms in Y is
(a) a substituted or unsubstituted and saturated or unsaturated aliphatic hydrocarbon residue or (b) a substituted or unsubstituted aromatic hydrocarbon residue comprising a six-member ring containing N atom therein, and Z is carboxyl group or a group derived therefrom or an aliphatic hydrocarbon residue having 1–4 carbon atoms, which is substituted or unsubstituted, (providing that Z represents a group other than COOCH$_3$ when X—Y is SO$_2$CH$_3$, and cystacyclin is excluded).

(11) The present invention relates to a 2,3-di-substituted cyclopentanone derivatives (except for cystacyclin) or a pharmacologically acceptable salt thereof in (9) mentioned above, wherein X is O or S.

(12) The present invention relates to a 2,3-di-substituted cyclopentanone derivatives (except for cystacyclin) or a pharmacologically acceptable salt thereof, wherein ,in (9) mentioned above, a hydrocarbon residue having 1–6 carbon atoms of Y is

[1] an alkyl group having 1–6 carbon atoms which is substituted or

[2] pyridino group or pyrimidinyl group which is substituted, and the number of substituents are one to three and the substituent on the alkyl group is selected from the group consisting of (i) carboxyl group or a group derived therefrom, (ii) amino group or a group derived therefrom, and (iii) hydroxy group or a group derived therefrom and the substituent on the pyridino group or pyrimidinyl group is a lower alkyl or a group described in the substituent on the said alkyl group and Z is carboxyl group or a group derived therefrom.

(13) The present invention relates to a 2,3-di-substituted cyclopentanone derivatives (except for cystacyclin) or a pharmacologically acceptable salt thereof, wherein ,in the substituent of Y in (11) mentioned above, (i) a carboxyl group or a group derived therefrom is a group shown as —COR$_1$; R$_1$ is —OR$_2$ or —NR$_3$R$_4$; R$_2$ is H or a hydrocarbon residue having 1–6 carbon atoms; R$_3$ or R$_4$ is H, an alkyl group having 1–6 carbon atoms or an acyl group having 1–20 carbon atoms respectively, (ii) an amino group or a group derived therefrom is a group shown as —NR$_5$R$_6$; R$_5$ or R$_6$ is H, an alkyl group having 1–6 carbon atoms or an acyl group having 1–20 carbon atoms respectively, (iii) a group derived from hydroxy group is a group shown as —OR$_7$; R$_7$ is hydrocarbon residue having 1–6 carbon atoms or an acyl group having 1–6 carbon atoms; and a group derived from carboxyl group in Z is a group shown as —COR$_8$ or —CHO R$_9$; and R$_8$ is independently same as R$_1$; R$_9$ is H, an alkyl group having 1–6 carbon atoms or acyl group having 1–20 carbon atoms.

(14) The present invention relates to a 2,3-di-substituted cyclopentanone derivatives or a pharmacologically acceptable salt thereof, in (12) mentioned above, wherein, in Y of (12) mentioned above, the substituent is at least a group selected from the group consisting of (i) a carboxyl group or an alkoxycarbonyl group having 1 to 6 carbon atoms, (ii) an amino group or an acylamino group, and (iii) hydroxy group or an alkoxy group having 1 to 6 carbon atoms, and, when the number of the substituents selected from these one are two or more, those substituents may be same or different groups, and Z is carboxyl group, an alkoxylcarbonyl group having 1–6 carbon atoms, hydroxymethyl group or an acyloxymethyl group having 1–20 carbon atoms.

(15) The present invention relates to a 2,3-di-substituted cyclopentanone derivative (except for cystacyclin) or a pharmacologically acceptable salt thereof wherein, in the general formula (I) of (1) mentioned above, (I) the group shown as —CH$_2$—X—Y is —CH2—S—CH$_2$—CH(OH)—CH$_2$OH and Z is —CH$_2$OCOCH$_3$, (II) the group shown as —CH$_2$—X—Y is —CH$_2$—S—CH$_2$—CH(COOH)NHCOCH$_3$ and Z is —CH$_2$OCOCH$_3$, (III) the group shown as —CH$_2$—X—Y is —CH$_2$—S—CH$_2$—CH(COOH)NHCOCH$_3$ and Z is —CH$_2$OH, (IV) the group shown as —CH$_2$—X—Y is —CH$_2$—S—CH$_2$—CH$_2$—NHCOCH$_3$ and Z is —CH$_2$OCOCH$_3$, (V) the group shown as —CH$_2$—X—Y is —CH$_2$—S—CH$_2$—CH$_2$—OH and Z is —CH$_2$OCOCH$_3$, (VI) the group shown as —CH2—X—Y is —CH$_2$-(3—COOCH$_3$)-pyridino and Z is —CH$_2$OH, (VII) the group shown as —CH2—X—Y is —CH$_2$—S—CH$_2$—CH(COOCH$_3$)NHCOCH$_3$ and Z is —COOH, (VIII) the group shown as —CH$_2$—X—Y is —CH$_2$—S—CH$_2$—CH(COOCH$_2$—CH=CH$_2$)NHCOCH$_3$ and Z is —COOH, (IX) the group shown as —CH$_2$—X—Y is —CH2—S—CH$_2$—CH(COOH)NHCOCH$_3$ and Z is —COOH, (X) the group shown as —CH$_2$—X—Y is —CH2—S—CH$_2$—CH(COOH)NHCOCH$_3$ and Z is —COOCH$_3$, (XI) the group shown as —CH$_2$—X—Y is —CH$_2$—S—CH$_2$—CH$_2$—NHCOCH$_3$ and Z is —COOCH$_3$, (XII) the group shown as —CH$_2$—X—Y is —CH$_2$—S—CH$_2$—CH$_2$—NHCOCH$_3$ and Z is —COOH, or (XIII) the group shown as —CH$_2$—X—Y is —CH$_2$—O—CH$_2$—CH(OH)—CH$_2$OH and Z is —CH$_2$OH,

(16) The present invention relates to a method for the production of a 2,3-di-substituted cyclopentanone derivative represented by the following general formula (Ia)

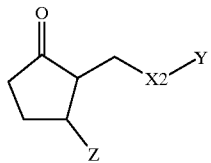

(Ia)

(wherein X$_2$ is S, O or NH; and Y and Z are the same described above) or a pharmacologically acceptable salt thereof characterized by reacting a reactive derivative of 2-hydroxymethyl group in the 2-hydroxymethyl-3-substituted cyclopentanone shown as the general formula (II)

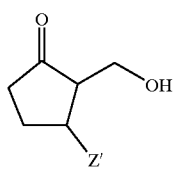

(II)

(wherein Z' is same as Z, and, when Z' has functional group, the functional group may be protected when necessary) (1-carbonyl group may be protected when necessary) (hereinafter referred to as merely the reactive derivative) with the compound shown as the general formula (III)

$$HX_2—Y \qquad (III)$$

(Wherein X2 and Y are same as defined above) and removing protecting group when necessary.

(17) The present invention relates to the method for the production according to (15) characterized by that the reaction is carried out in an inert organic solvent at a temperature between 0° C. and the boiling point of the solvent.

(18) The present invention relates to the method for the production of a 2,3-di-substituted cyclopentanone derivative or a pharmacologically acceptable salt thereof according to (15) mentioned above, wherein the reactive derivative is a 3-substituted-2-methylenecyclopenetanone derivative shown as the general formulae (IV), (V), (VI) or (VII)

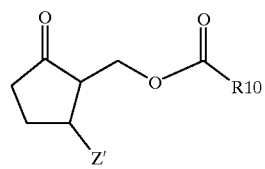

(IV)

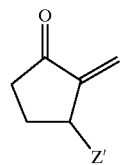

(V)

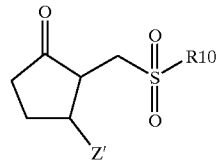

(VI)

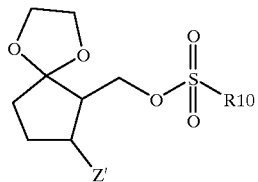

(VII)

(wherein R$_{10}$ is a hydrocarbon residue having 1–10 carbon atoms; and Z' is the same as Z and the functional group is protected when necessary).

(19) The present invention relates to a method for the production of a (1R, 2S)-2-[( (2R)-2-protected or unprotected amino-2-carboxy ethyl) thiomethyl]-3-oxo-1-cyclopentanecarboxylic acid or an alkyl ester thereof or a pharmacologically acceptable salt thereof characterized by reacting N-protected-L-cysteine with a (2S,3R)-3-carboxy-2-sulfonylmethyl-cyclopentanone derivative shown as the general formula (XII)

(XII)

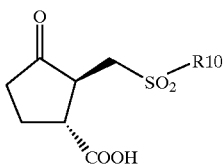

(wherein $R_{10}$ is an hydrocarbon residue having 1 to 9 carbon atoms which may be substituted, and, when the residue is substituted, the substituent may be one or a combination of two or more members selected from the group consisting of halogen atoms, nitro group, cyano group, hydroxy group, amino group, carboxyl group, an alkoxycarbonyl group having 1–9 carbon atoms, and an aryl group and these substituent may be protected when the substituent is a functional group), a salt thereof, or an alkyl ester thereof, or 2-methylidene-3-oxo-1-cyclopentanecarboxylic acid shown as the general formula (V')

(V')

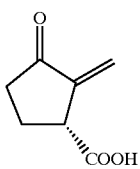

or a salt thereof or an alkyl ester thereof, and removing the protective group when necessary.

(20) The present invention relates to 3-substituted-2-methylene cyclopentanone derivative shown as the following general formula (IV), (V), (VI) or (VII)

(IV)

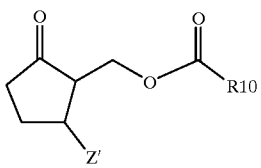

(V)

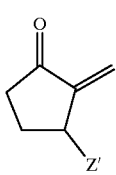

(VI)

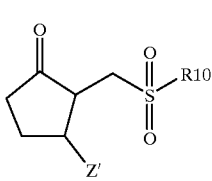

(VII)

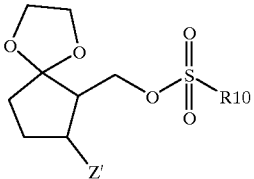

(wherein $R_{10}$ is a hydrocarbon residue having 1–10 carbon atoms; and Z' is same as Z providing that the functional group thereof is protected when necessary), except that Z' is COOH or COOCH$_3$ in the general formula (V), and that Z' is COOH or COOCH$_3$ and $R_{10}$ is methyl or phenyl in the general formula (VI) or a pharmacologically acceptable salt thereof.

(21) The present invention relates to (2S, 3R)-3-protected hydroxymethyl-2-thiomethyl cyclopentanone derivative shown as the following general formula (XI)

(XI)

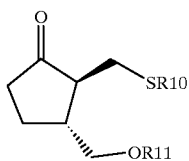

(wherein $R_{11}$ is protective group of hydroxy group and $R_{10}$ is same as mentioned above) or a salt thereof,

(22) The present invention relates to an accelerator of differentiation of neurons or a pharmceutical composition characterized by containing a cyclopentanone derivative which has at least one substituted lower alkyl group as a substituent on the ring of cyclopentanone and which has activity for acceleration of differentiation of neurons, or a pharmacologically acceptable salt thereof as ingredient.

BEST MODE FOR CARRYING OUT THE INVENTION

The expression "an activity for accelerating differentiation of neuron" as used in this invention means the activity for elongating nerve-like apophysises manifested on the PC 12 cells by the method of testing to be described hereinafter.

The cyclopentanone derivative of the present invention having at least one substituted lower alkyl group as a substituent on the ring of cyclopentanone is not limited in the number of substituent, the kind of substituent and the kind of substituent on the said lower alkyl group, if it has the activity for accelerating differentiation of neurons.

The number of substituents is suitably two or more generally, and the position of substitution is suitably 2 or 3 on the ring of the cyclopentanone. The position of substitution of said substituted lower alkyl group on the ring of cyclopentanone is not limited especially, and preferably the position of substitution is 2 on the ring of the cyclopentanone.

The lower alkyl group of said substituted lower alkyl group is the group which is removed at least two hydrogen atoms from the saturated or unsaturated, and straight chained or branched hydrocarbon group having 1 to 6 carbon atoms, for example, methylene group, ethylene group, 1,2-propylene group, 1,3-propylene group and so on, suitably methylene group. And the substituent of the said substituted lower alkyl group is suitably the substituent shown as Y—X— (wherein Y, X is same means as mentioned above).

When the cyclopentanone derivative has a said substituted lower alkyl group as a substituent on the position 2 of the cyclopentanone ring, it is suitably a cyclopentanone derivative having further substituent in the position 3 therein. The Z group, wherein Z is same means as mentioned above, as the substituent of position 3 is preferred.

The term "hydrocarbon residue" as used in this invention means the group which remains after removal of one hydrogen atom from a saturated or unsaturated hydrocarbon (which, when it is cyclic, may contain one or more heteroatoms).

Such groups of the upper level of conceptual hierarchy as, for example, hydrocarbon residues, aliphatic hydrocarbon residues, alkyl groups, alkenyl groups, aromatic cyclic groups, acyl groups, amino groups, alkylamino groups, acylamino groups, alkoxy groups, and alkoxycarbonyl groups etc. which are used in this invention are used in the sense of embracing both groups of an unsubstituted group and a group having one or more substituents unless otherwise specified.

The substituted or unsubstituted hydrocarbon residue containing 1 through 6 carbon atoms and having total molecular weight of not less than 15 and not more than 400 which is represented by Y in the general formula (I) mentioned above may be chain, cyclic, saturated, or unsaturated. The hydrocarbon residue, when cyclic group, may contain such heteroatoms as oxygen, nitrogen, and sulfur etc. in the ring thereof. Though this hydrocarbon residue may be substituted or unsubstituted, it is preferred to contain one or more substituents from the viewpoint of physiological activity.

When the hydrocarbon residue is an unsubstituted aliphatic hydrocarbon residue, it may be straight chain, branched, saturated, unsaturated, or cyclic. As examples of the chain or cyclic hydrocarbon residue of 1–6 carbon atoms, (1) alkyl groups such as methyl, ethyl, propyl, isopropyl, butyl, isobutyl, pentyl, 2-methyl-butyl, and hexyl etc., (2) alkenyl groups such as vinyl group and allyl group etc., and (3) cyclo alkyl groups such as cyclopentyl, cyclohexyl, and piperidinyl etc. may be cited. Generally, these hydrocarbon residues are preferred to be a chain. As examples of the substituted aliphatic hydrocarbon residue, such groups as are substituted by 1–4, preferably 1–3, and more preferably 1–2 substituents on such unsubstituted alkyl, alkenyl, or cyclic groups as mentioned above may be cited. The substituents have no particular restriction, except a group which deprive physiological activity of the compound of this invention. The total molecular weight of the group represented by Y including the substituent is not more than 400, preferably not more than 300, and more preferably not more than 150.

Examples of the substituent are, (i) carboxyl group and groups derived therefrom, (ii) amino group and groups derived therefrom, (iii) hydroxy group and groups derived therefrom, and (iv) halogen atoms etc.

The groups which are derived from the carboxyl group stated in (i) above include (1) aldehyde groups obtained by reducing the carboxyl group and (2) groups resulting from esterifying or amidating the carboxyl group and the nitrile group obtained by further oxidizing the amide group, for example. As the carboxyl group and the groups derived therefrom which are appropriate as the substituent mentioned above, the groups represented by —$COR_1$ are cited, wherein $R_1$ is an alkoxy group represented by the general formula of —$OR_2$ (wherein $R_2$ is a hydrocarbon residue of 1 through 6 carbon atoms which may be substituted) or an unsubstituted or substituted amino group represented by the general formula of —$NR_3R_4$ (wherein $R_3$ and $R_4$ are independently a hydrogen atom, an alkyl group of 1 through 6 carbonatoms which may be substituted, or an acyl group of 1 through 20 carbon atoms which may be substituted). The hydrocarbon residueof 1 through 6 carbon atoms which may have one or more substituents in $R_2$ is the same as that which has been already described with respect to the group represented by Y.

The alkyl group of 1 through 6 carbon atoms in $R_3$ and $R_4$ are the same as those already cited with respect to the aliphatic hydrocarbon residue. The acyl groups of 1 through 20 carbon atoms in $R_3$ and $R_4$ include acetyl, mono, di, or trihalogenoacetyl, propionyl, butanoyl, pentanoyl, heptanoyl, heptadecanoyl, benzoyl, and halogenobenzoyls etc.. The hydrocarbon residue of 1 through 20 carbon atom which is bound to the carbonyl group may be chain, branched, or cyclic and may be substituted. In these groups, acyl groups of 1 through 6 carbon atoms are preferable, acyl groups of 1 through 3 carbon atoms are more preferable, and acetyl group is most preferable. The substituent may be the same as those already described with respect to the aliphatic hydrocarbon residue.

As the amino group or the group derived from the amino group in (ii) mentioned above, (1) amino groups, mono or di-substituted amino groups represented by the general formula —$NR_5R_6$ (wherein $R_5$ and $R_6$ may be identical or different and are each a hydrogen atom, an alkyl group of 1 through 6 carbon atoms which may be substituted, or an acyl group of 1–20 carbon atoms which may be substituted) and (2) the nitro group obtained by the oxidation of the amino group may be cited. The specified examples of $R_5$ and $R_6$ are the same as those already cited with respect to $R_3$ and $R_4$.

The groups derived from the hydroxyl group in (iii) mentioned above include the groups which are obtained by alkylation or acylation of the hydroxyl group, for example. The example is the groups which is represented by the general formula of —$OR_7$ (wherein $R_7$ is an hydrocarbon residue of 1 through 6 carbon atoms which may be substituted or an acyl group of 1 through 20 carbon atoms which may be substituted). As the hydrocarbon residue or the acyl group in $R_7$, the same as those already mentioned with respect to the group represented by Y may be cited.

The halogen atoms include chlorine, fluorine, and bromine etc.

Typical examples of the substituent in these aliphatic hydrocarbon residue of 1 through 6 carbon atoms are carboxyl, an alkoxycarbonyl of 1 through 4 carbon atoms, amino, an acylamino of 1 through 4 carbon atoms, halogen-substituted acylamino of 1 through 4 carbon atoms, and hydroxy. In the acylamino groups, groups such as acetylamino and trifluoroacetylamino etc. are preferable. In the alkoxycarbonyl groups, groups such as methoxycarbonyl, ethoxycarbonyl, propoxycarbonyl and allyloxycarbonyl etc. are preferable.

When the hydrocarbon residue of 1 through 6 carbon atoms is an aromatic hydrocarbon, that may be carbon-cyclic or hetero-cyclic aromatic hydrocarbon, usually, such as unsaturated cyclic hydrocarbons of 5 or 6 carbon atoms. Those examples are phenyl, pyridyl, pyrimidyl, piradinyl and pyrolyl etc. These may contain one or more substituents. Examples of the substituent are the aliphatic hydrocarbon residues of 1 through 6 carbon atoms and the same substituent used in Y mentioned above.

Preferably, the group represented by Y is an alkyl group having 1 through 4 carbon atoms and containing one or two substituents. The substituent is selected from the group consisting of (i) carboxyl group or alkoxycarbonyl groups, (ii) amino group or acylamino groups, and (iii) hydroxyl group or alkoxy groups. When there are two substituents in the alkyl group, they may be identical with or different from each other. As the "alkyl group" and "acyl group" which are mentioned in these groups, those already described may be used herein without change. Examples of the alkoxy group are such saturated or unsaturated groups which have 1 through 6 carbon atoms as methoxy, ethoxy, propoxy, butoxy, pentoxy, hexoxy, and allyloxy etc., and preferably those of 1 through 4 carbon atoms may be cited.

Preferable examples of the group represented by Y are as follows: 2-carboxyethyl group, 2-hydroxyethyl group, 2-aminoethyl group, 2-acetyl-aminoethyl group, 3-hydroxypropyl group, 3-carboxypropyl group, 3-methoxycarbonylpropyl group, 2-carboxy-2-acetylaminoethyl group, 2-carboxy-2-aminoethyl group, 2-carboxy-2-trifluoroacetyl aminoethyl group, 2-carboxy-2-pentadecanoylaminoethyl group, 2-methoxycarbonyl-2-acetyl-aminoethyl group, 2-ethoxycarbonyl-2-acetylaminoethyl group, 2-propoxycarbonyl-2-acetylaminoethyl group, 2-allyloxycarbonyl-2-acetyl-aminoethyl group, and 2,3-dihydroxy propyl group.

In the examples of X in the general formula (I), S, O, SO, or $SO_2$ are preferable and S or O is most general.

Preferred examples of the group represented by —X—Y in the general formula (I) are an alkylthio of 1 to 4 carbon atoms which may have one or two substituents, an alkylsulfinyl of 1 to 4 carbon atoms which may have one or two substituents, an alkylsulfonyl of 1 to 4 carbon atoms which may have one or two substituents, an alkoxy of 1 to 4 carbon atoms which may have one or two substituents and an alkylamino of 1 to 4 carbon atoms which may have one or two substituents, and pyridylthio having one or two substituents on the ring thereof and pyrimidinylthio having one or two substituents on the ring thereof. More preferable examples thereof are an alkylthio or alkoxy group of two or three carbon atoms which have one or two substituents selected from the group consisting of (1) hydroxy, (2) ($C_1$–$C_4$) alkoxy, (3) amino, (4) ($C_1$–$C_4$) acylamino, (5) carboxy, and (6) ($C_1$–$C_4$) alkoxycarbonyl.

More preferable examples thereof are 2-(carboxy or an alkoxycarbonyl of 1 through 3 carbon atoms)-2-(amino or acetylamino)-ethylthio or -ethoxy group and 2-(amino or acetylamino)-ethylthio or -ethoxy group, 2-hydroxyethylthio or -ethoxy group, and 2,3-dihydroxy-propylthio or -propoxy group.

Examples of the carboxyl group or the group derived therefrom in Z of the general formula (I) are those already described with respect to the substituents in Y mentioned above and the groups represented by —$CH_2OR_9$ (wherein $R_9$ is a hydrogen atom, an alkyl group of 1 through 6 carbon atoms which may be substituted, or an acyl group of 1 through 20 carbon atoms which may be substituted). Examples of the aliphatic hydrocarbon residue of 1 through 4 carbon atoms in Z, which is substituted or unsubstituted, are those hydrocarbon residues of 1 through 4 carbon atoms already described in the part of Y may be cited.

Preferred examples of Z are the groups represented by —$COR_8$ or —$CH_2OR_9$, wherein independently from $R_1$, $R_8$ has the same meaning as $R_1$ and $R_9$ has the same meaning as defined above.

More preferred examples of Z are a carboxyl group, an alkoxycarbonyl group, hydroxymethyl group, and acyloxymethyl group may be cited. The terms "alkoxy" and "acyl" used in these groups have the same meanings as already described with respect to the alkoxy group and the acyl group. Among the groups cited above as examples of Z, carboxy group, hydroxymethyl group, and acyloxymethyl group of 1 through 3 carbon atoms are more preferable.

Typical compounds represented by the general formula (I) of this invention are following compounds of (I) to (XVI). The present compounds are not limited to the typical compounds.

(I) 3-Acetoxymethyl-2-[(2,3-bishydroxypropyl)thiomethyl]-cyclopentanone (II) 3-Acetoxymethyl-2-[(2-acetylamino-2-carboxyethyl)thio methyl]-cyclopentanone (III) 2-[(2-Acetylamino-2-carboxyethyl) thiomethyl]-3-hydroxy-methylcyclopentanone (IV) 3-Acetoxymethyl-2-[(2-acetylaminoethyl)thiomethyl]cyclopentanone (V) 3-Acetoxymethyl-2-[(2-hydroxyethyl)thiomethyl]cyclopentanone (VI) 3-Hydroxymethyl-2-[(3-methoxycarbonylpyridin-2-yl)-thio-methyl]-cyclopentanone (VII) 2-[(2-Acetylamino-2-methoxycarbonylethyl)thiomethyl]-3-oxo-1-cyclopentanecarboxylic acid (VIII) 2-[(2-Acetylamino-2-allyloxycarbonylethyl)thiomethyl]-3-oxo-1-cyclopentanecarboxylic acid (IX) 2-[(2-Acetylamino-2-carboxyethyl)thiomethyl]-3-oxo-1-cyclopentanecarboxylic acid (X) 2-[(2-Acetylamino-2-carboxyethyl) thiomethyl]-3-methoxy-carbonylcyclopentanone (XI) 2-[(2-Acetylaminoethyl)thiomethyl]-3-methoxycarbonylcyclo-pentanone (XII) 2-[(2-Acetylaminoethyl)thiomethyl]-3-oxo-1-cyclopentane carboxylic acid (XIII) 2-[2,3-Bis(hydroxypropyl)oxymethyl]-3-hydroxymethylcyclopentanone (XIV) 2-[N-(2-acetylamino-2-carboxyethyl) aminomethyl]-3-hydroxymethylcyclopentanone (XV) 2-[(2-Acetylamino-2-methoxycarbonylethyl) thiomethyl]-3-methoxycarbonylcyclopentanone (XVI) 3-Hydroxymethyl-2-[(6-methylpyridin-2-yl) thiomethyl]-cyclopentanone (I') (2S,3R)-3-Acetoxymethyl-2-[(2RS)-(2,3-dihydroxypropyl) thiomethyl]-cyclopentanone The typical compounds mentioned above are shown in the following table 1 using the general formula (I). In the formulas, Ac represents acetyl group and Me represents methyl group.

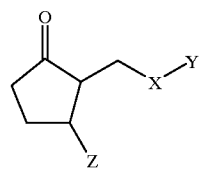

(I)

TABLE 1

| No. | X | Y | Z |
|---|---|---|---|
| (I) | S | CH₂CH(OH)CH₂OH | CH₂OAc |
| (II) | S | CH₂CH(NHAc)COOH | CH₂OAc |
| (III) | S | CH₂CH(NHAc)COOH | CH₂OH |
| (IV) | S | CH₂CH₂NHAc | CH₂OAc |
| (V) | S | CH₂CH₂OH | CH₂OAc |
| (VI) | S | 3-Methoxycarbonyl pyridin-2-yl | CH₂OH |
| (VII) | S | CH₂CH(NHAc)COOMe | COOH |
| (VIII) | S | CH₂CH(NHAc)COOCH₂CH=CH₂ | COOH |
| (IX) | S | CH₂CH(NHAc)COOH | COOH |
| (X) | S | CH₂CH(NHAc)COOH | COOMe |
| (XI) | S | CH₂CH₂NHAc | COOMe |
| (XII) | S | CH₂CH₂NHAc | COOH |
| (XIII) | O | CH₂CH(OH)CH₂OH | CH₂OH |
| (XIV) | NH | CH₂CH(NHAc)COOH | CH₂OH |
| (XV) | S | CH₂CH(NHAc)COOMe | COOMe |
| (XVI) | S | 6-Methylpyrimidin-2-yl | CH₂OAc |

The compound of the present invention contains one or more asymmetric carbon atom in the ring of cyclopentanone and in the substituent thereof. Accordingly, the present compound contains also an optically active substance and racemic substanc. It is suitable that the present compound is used as the optically active substance. In the present specification, the configuration of asymmetric carbon atom is shown as R or S.

The compound which has S, O, or NH for X in the formula (I) of this invention can be obtained by causing a compound represented by the following general formula (III)

$$HX_2\text{—}Y \quad (III)$$

(wherein $X_2$ is S, O, or NH and Y has the same meaning as defined above) to react with a reactive derivative of the 2-hydroxymethyl group of a 2-hydroxymethyl-3-substituted cyclopentanone (the carbonyl group at the 1 position thereof may be protected when necessary) represented by the general formula (II)

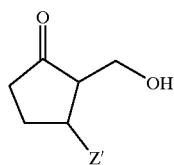

(II)

(wherein Z' has the same meaning as Z, provided that when the group contains a functional group, the functional group may be protected when necessary)(hereinafter refer to as the reactive derivative ) and optionally removing the protective group. When the compound of $HX_2$—Y of the general formula(III)contains an asymmetric carbon atom, the optically active substance thereof can be used to obtain a corresponding optically active compound.

Any method which is capable of condensing the both compounds can be used for the reaction. Generally, this reaction is carried out in an inert organic solvent under mild conditions such as, for example, at a temperature in the range of from −10 centigrade temperature to the boiling point of the solvent, preferably between 0° C. and 90° C. When the compound of the general formula (III) is a thiol compound, the temperature in the approximate range of from 10° C. to 50° C. are more appropriate. The reaction of the compound of the general formula (II) and the compound of the general formula (III) may be carried out in equivalent amount. Actually in the reaction, the compound of the general formula (III) may be used in an excess amount (1 to 2 mols per one mol of the compound of the general formula (II), for example). The compound which has SO or $SO_2$ for X in the general formula (I) can be obtained by subjecting a compound having S for X to oxidation by the conventional method thereby converting S into SO or $SO_2$.

Preferred examples of the reactive derivative mentioned above are the compounds of the following general formulas (IV), (V), (VI) and (VII).

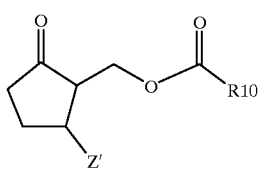

(IV)

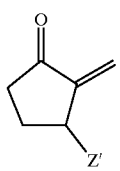

(V)

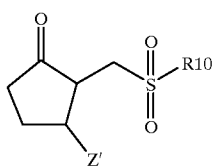

(VI)

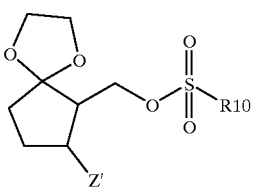

(VII)

(wherein, $R_{10}$ is a hydrocarbon residue having 1 to 10 carbon atoms such as, for example, an alkyl group, an alkenyl group, or aryl group, which may be substituted or unsubstituted. When the substituent is a functional group, it may be protected by a protective group when necessary. Z' has the same meaning as mentioned above.)

The hydrocarbon residue containing 1–10 carbon atoms shown as $R_{10}$ is not limited particularly provided that an elimination group is formed, for example, any of the examples already cited with reference to Y can be used without any change. As examples of the unsubstituted alkyl group of 1–10 carbon atoms, methyl group, ethyl group, isopropyl group, t-butyl group, and pentyl group etc. may be cited. The substituent of the substituted alkyl group may be any of the examples of the substituent on the hydrocarbon residue mentioned above. As examples thereof, halogen atoms, nitro group, cyano group, hydroxyl group, amino group, carboxyl group, or alkoxycarbonyl groups of 1 through 9 carbon atoms and aryl group may be cited. These groups may be present either singly or in a combination of two or more members. When the substituent is a functional group, it may be protected with a protective group. Aryl group and alkenyl group etc. also may be cited as the hydrocarbon group of 1–10 carbon atoms represented by $R_{10}$. For example, p-methylphenyl group etc. may be cited as a substituted aryl group. A preferred examples as the hydrocarbon group containing 1–10 carbon atoms shown as $R_{10}$ are methyl group, ethyl group, 2,3-isopropylidenedioxypropyl group, and p-methylphenyl group may be cited.

When Z' is hydroxymethyl group and so on, the protective group for the hydroxy group is an acyl group of 1 through 20 carbon atoms and an alkylsilyl group of 1 through 6 carbon atoms. Occasionally, an alkyl group of 1 through 6 carbon atoms or a substituted or unsubstituted benzyl group etc. is usable. Trimethyl silyl group, t-butyldiphenylsilyl group, and t-butyldimethyl silyl group may be cited as preferable alkylsilyl group.

Any of the protective groups for the hydroxy group mentioned above are usable as the protective group for functional groups other than hydroxy group, for example, carboxyl group etc. In the case of an amino group, the same protective groups except alkylsilyl groups are able to be used . The term "acyl group" as used in the specification hereof is to be construed as embracing such alkoxycarbonyl groups as butoxy carbonyl or benzyloxy carbonyl unless any hindrance is incurred.

As examples of the compounds represented by the general formula (IV), (V), (VI), and (VII), the following compounds may be cited, for example.

(a) 2,3-Bis(acetoxymethyl) cyclopentanone
(b) 3-Acetoxymethyl-1-methylidene cyclopentanone
(c) 2-[(2,3-isopropylidenedioxypropyl)sulfonylmethyl]-3-oxo-1-cyclopentane carboxylic acid
(d) 2-[(2,3-isopropylidenedioxypropyl) sulfonylmethyl]-3-methoxycarbonylcyclopentanone
(e) 3-(t-Butyldimethylsilyloxymethyl)-1,1-ethylenedioxy-2-mesyl-oxymethylcyclopentane
(f) 2-methylidene 3-oxo-1-cyclopentanecarboxylic acid
(g) 3-Methoxycarbonyl-2-methylidenecylcopentanone The compounds (a) and (b) can be produced as follows.

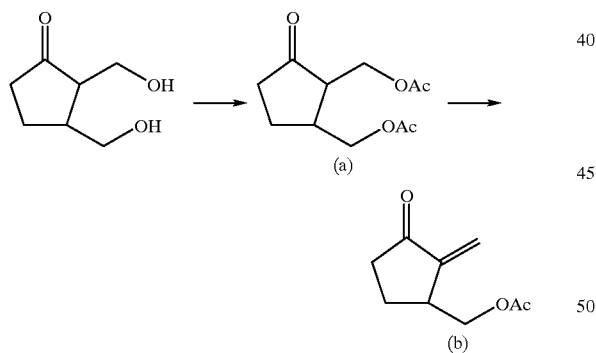

The compound (a) can be obtained by acetylating 2,3-bis-(hydroxymethyl) cyclopentanone and the compound (b) can be easily produced by treating the compound (a) with a base or such a strong basic amine as triethylamine.

The starting raw material, i.e. 2,3-bis(hydroxymethyl) cyclo-pentanone, is a substance known in literatures and can be produced by the method disclosed in JP-A-05-1044 or a method with necessary modifications thereto.

Optical isomer (2S,3R)-2,3-bis(hydroxymethyl) cyclo-pentanone can be obtained by optical resolution of optically inactive one by chromatography and so on for optical resolution. Furthermore, the compound protected by acyl group of the (2S,3R) form can be obtained by the method disclosed in JP-A-08-231469, too.

The compounds (c) and (d) can be produced as follows.

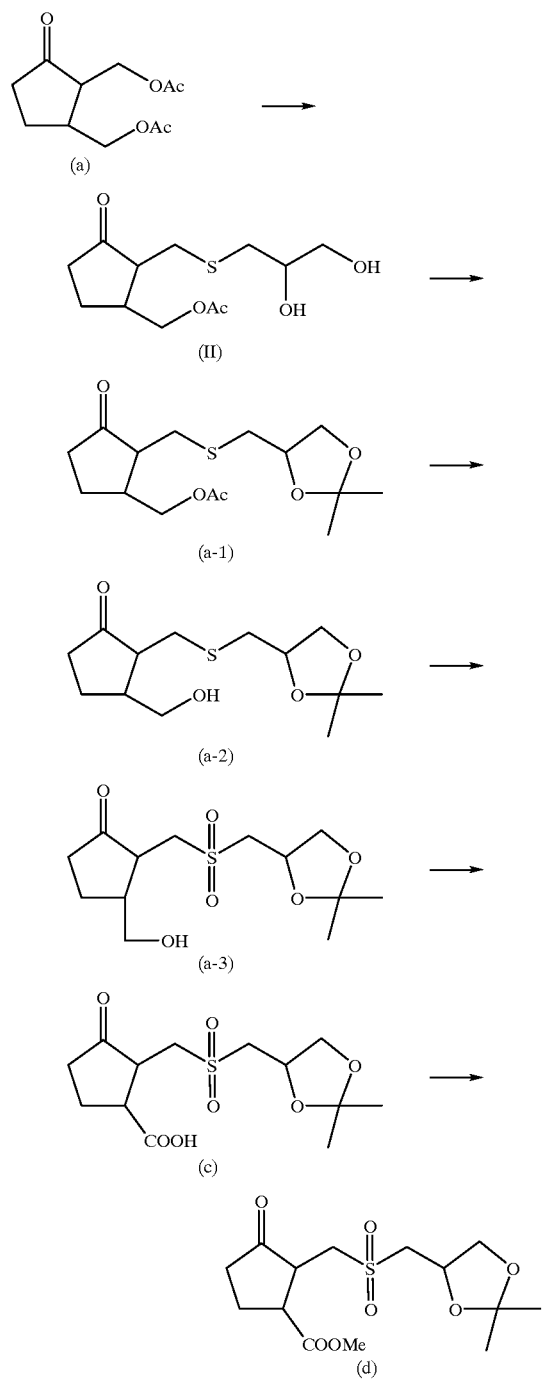

A compound (a-1) can be obtained by causing the compound (a) to react with thioglycerin in the presence of one equivalent amount of an alkali thereby deriving a compound (II), then converting the two hydroxyl groups of the compound (II) into isopropylidene . Subsequently a compound (a-2) can be obtained by alkali treating the compound (a-1) thereby removing the acetyl group. A compound (a-3) can be obtained by oxidizing the sulfide of the compound (a-2) into sulfone. A compound (c) can be produced by oxidizing the hydroxymethyl group of the compound (a-3) in the position 3. The compound (d) can be produced by esterifying the carboxylic acid of the compound (c).

The compound (e) can be produced as follows. In the formulas, Ac represents acetyl group and TBDMS represents t-butyldimethyl silyl group.

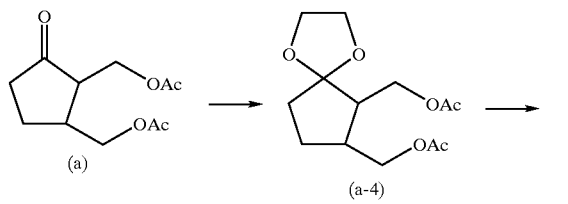

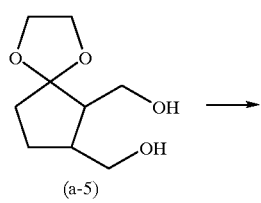

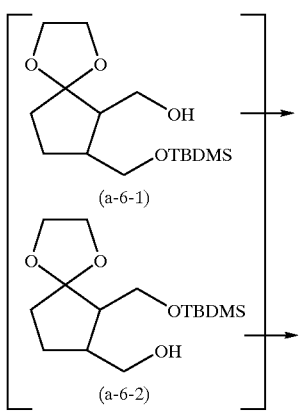

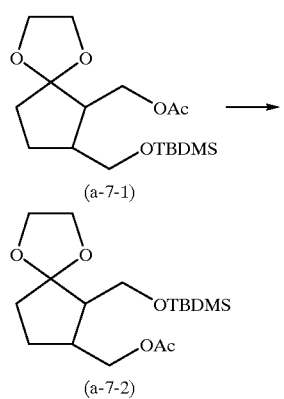

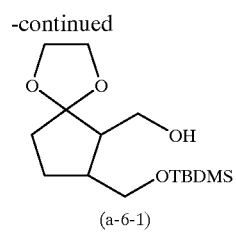

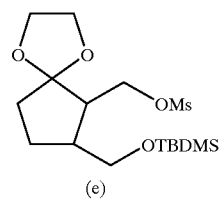

The compound (a) is converted into ketal by the conventional method of ketalation to obtain a compound (a-4) and the acetoxy group is saponified to obtain a diol compound (a-5). The mono-silylation of the compound (a-5) affords a mixture of a compound (a-6-1) of which the 3 position is silylated and a compound (a-6-2) of which the 2 position is silylated. When this mixture is directly acylated, it produces a mixture of a compound (a-7-1) and a compound (a-7-2). The mixture of a compound (a-7-1) and a compound (a-7-2) can be separated into the component compounds by chromatography. The compound (a-7-1) is separated by this. Then, the obtained compound (a-7-1) is saponified to isolate a compound (a-6-1). By mesylating the hydroxyl group of the produced compound(a-6-1), the compound (e) can be produced.

The compound of the general formula (VII) which has a carboxyl group for Z' can be obtained by removing the Ac group of the compound (a-7-2) by the conventional method, oxidizing the resultant hydroxymethyl group into a carboxyl group by the conventional method, removing TBDMS, and mesylating the hydroxyl group of the resultant compound.

The compounds (f) and (g) can be obtained by hydrolyzing the compounds (c) and (d) with such an alkali as sodium hydroxide etc.

The compounds of the general formulas (IV) through (VII) other than the compounds (a) through (g) mentioned above can be produced by suitably following the aforementioned procedures for the production of the compounds (a) through (g).

The production of the compounds represented by the general formula (I) will be described more specifically below.

(1) Method for the production of a compound having S for X in the general formula (I)

A compound having S for X can be obtained by causing a mercapto compound represented by the general formula (VIII)

$$HS-Y \qquad (VIII)$$

(wherein Y has the same meaning as defined above) to react with the reactive derivative mentioned above, preferably a compound represented by the general formula (IV), (V), or (VI) in water, an alcohol type solvent such as methanol, ethanol, or propanol, a water-soluble solvent such as acetone, tetrahydrofuran, or dimethyl formamide, or a mixture of the solvents mentioned above, preferably a water-methanol mixed solvent, a water-acetone mixed solvent, or a water-methanol-acetone mixed solvent, adding an alkali, e.g. an alkali metal hydroxide or an alkali metal salt of a weak acid such as, for example, potassium hydroxide, sodium hydroxide, potassium carbonate, or sodium carbonate at a temperature in the approximate range of from −10° C. to the boiling point of the solvent, preferably between 0° C. and 50° C. and removing a protective group when necessary.

The compounds represented by the general formula (VIII) are mercaptan compounds having a substituent Y mentioned above. More specifically, substituted or unsubstituted aliphatic hydrocarbon mercaptan compounds of 1 through 6, preferably 2 through 4, carbon atoms or substituted and unsubstituted aromatic hydrocarbon (optionally containing one or two hetero-atoms) mercaptan compounds of 4 through 6 carbon atoms may be cited. Preferable examples are alkyl mercaptans containing 2 through 4 carbon atoms and having one or two substituents. Examples of the substituent are hydroxy groups, lower alkoxy groups, carboxy groups, lower alkoxycarbonyl groups, amino group, and mono or di-substituted amino groups, one or two hydrogen atoms of amino group being substituted with an alkyl group or an acyl group. These substituents may be protected when necessary. As the lower alkoxy groups, saturated or unsaturated alkoxy groups of 1 through 6, preferably about 1 through 4, carbon atoms may be cited. Generally, the number of carbon atoms in the alkyl group or the acyl group is in the approximate range of 1 to 16.

Typical examples of the compounds represented by the general formula (VIII) include ethyl mercaptan, propyl mercaptan, butyl mercaptan, mercaptoethanol, 3-mercaptopropanol, alpha-thio glycerin, methoxyethyl mercaptan, mercaptoacetic acid, mercapto propionic acid, methoxycarbonyl ethylmercaptan, aminoethyl mercaptan, 3-aminopropyl mercaptan, acetylaminoethyl mercaptan, methylaminoethyl mercaptan, 1-acetylamino-2-mercapto propionic acid (N-acetylcysteine), 2-acetylamino-2-methoxy-carbonyl ethyl mercaptan (N-acetylcysteine methyl ester), 2-acetyl amino-2-allyloxycarbonyl ethyl mercaptan (N-acetylcysteine allyl ester), 3-methoxycarbonyl-2-mercaptopyridine etc.

(2) Method for the production of a compound having SO or $SO_2$ for X in the general formula (I)

This compound is obtained by oxidation according to the conventional method of the compound having S for X in the general formula (I) which is obtained as described above.

For example, the compound having $SO_2$ for X is obtained by oxidizing the compound having S for X in an inert solvent, for example, a halogenated hydrocarbon solvent etc. such as dichloromethane etc. with such an oxidizing agent as m-chloroperbenzoic acid etc. The compound having SO for X is obtained by treating the compound having S for X with hydrogen peroxide in a water-soluble solvent such as acetic acid.

Though the reaction temperature is not particularly restricted, the reaction is carried out generally at a temperature in the approximate range of −20° C. to 50° C., preferably −5° C. to 10° C. When the functional group is protected, the protection of the protected group is removed when necessary.

(3) Method for the production of a compound having 0 for X in the general formula (I)

This compound is obtained generally by allowing a 1,1-ethylene dioxy-3-protected hydroxymethyl or protected carboxyl-2-alkylsulfonyl-oxymethylcyclopentane represented generally by the general formula (VII) to condense in an inert solvent with an alcohol represented by the general formula (IX)

H O—Y (IX)

(wherein Y has the same meaning as defined above) after convertion of the said alcohol to the alcoholate thereof and to remove the protective group when necessary.

As the inert solvent, a substituted or unsubstituted hydrocarbon solvent having no reactive group such as hydroxy group is generally used. Aromatic solvents such as, for example, benzene, toluene, and xylene etc.are used, and benzene is preferably used. The reaction is carried out generally in the approximate range of from 0° C. to the boiling point of the solvent, preferably from 20° C. to 90° C.

The alcoholate compound of the alcohol of the general formula (IX) mentioned above can be easily obtained by the conventional method, for example, by causing the alcohol to react in the reaction solvent mentioned above with an alkali metal hydride such as sodium hydride or potassium hydride.

As examples of the alcohol represented by the general formula (IX), substituted or unsubstituted alcohols of 1 through 6 carbon atoms are cited. They may be saturated or unsaturated aliphatic or aromatic alcohols. The substituent in the substituted alcohols may be any of the examples of the substituent already cited with respect to the mercapto compound.

The typical alcohols represented by the general formula (IX) are methanol, ethanol, propanol, butanol, ethylene glycol, propylene glycol, glycerin, 3-acylaminopropanol, and 2-acylamino-2-carboxyethylalcohol.

(4) Method for the production of a compound having NH for X in the general formula (I)

This compound can be obtained, similarly to the method of (3) mentioned above, by causing a reactive derivative represented by the general formula (VII) to react with an amine represented by the general formula (X)

$H_2N$—Y (X)

(wherein Y has the same meaning as defined above) in an inert solvent, under heating and refluxing when necessary, and removing a protective group when necessary.

As examples of the amine represented by the general formula (X), amines having substituted or unsubstituted hydrocarbon residues containing 1 through 6 carbon atoms may be cited. They may be saturated or unsaturated aliphatic or aromatic amines. The substituent may be any of the examples already cited with respect to the mercaptan compound. Also, the compounds of which OH is changed into $NH_2$, cited above as examples of the alcohol of the general formula (IX), can be cited.

The configuration of the substituents at the 2 position and the 3 position of 2,3-di-substituted cyclopentanone derivatives represented by the general formula (I) which is obtained as described above may be either cis or trans form. Generally, the trans form is preferred. When this cyclopentanone derivatives forms a salt with an acid or a base, the salt is also comprised. When the compound of the general formula (1) forms a hydrate, the hydrate is also comprised.

When obtaining an optically active compound from an optically inactive compound, the optically active compound can be obtained by optical resolution of the optically inactive compound by means of the chromatography etc. adapted for optical resolution. The optical resolution may be conducted in the final step or in a step of intermediate thereof.

The optical compound can be synthesized by using an optically active raw material by following the procedure for the synthesis of cystacyclin which will be described hereinafter with necessary modifications.

Synthesis of cystacyclin and synthesis of intermediate thereof:

A (1R, 2S)-2-[(2R)-(2-protected or unprotected amino-2-carboxy)ethylthio] methyl-3-oxo-1-cyclopentanecarboxylic acid or a pharmacologically acceptable salt thereof (cystacyclin when the protective group of the amino group is acetyl group) can be synthesized by optionally protecting the functional group of a (2S, 3R)-3-protected hydroxymethyl-2-thiomethylcyclopentanone derivative represented by the following general formula (XI)

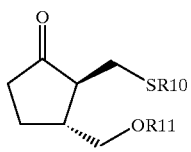

(XI)

(wherein $R_{11}$ is the protective group for a hydroxy group and $R_{10}$ has the same meaning as defined above) or a salt thereof, then selectively removing the protective group of the protected hydroxymethyl group at the 3 position, next oxidizing the thiomethyl group at the 2 position into a sulfonyl methyl group, subsequently oxidizing the hydroxymethyl group at the 3 position into carboxyl group thereby obtaining a (2S, 3R)-3-carboxy-2-sulfonylmethylcyclopentanone derivative represented by the following general formula (XII)

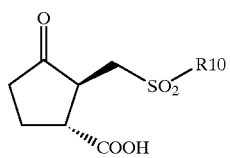

(XII)

(wherein $R_{10}$ has the same meaning as defined above) or a salt thereof, causing an N-protected-L-cysteine to react with the obtained derivative or salt thereof, and optionally removing the protective group.

A (2S, 3R)-3-protected hydroxymethyl-2-thiomethylcyclopentane derivative represented by the aforementioned general formula (XI) or a salt thereof can be synthesized as follows.

The (2S, 3R)-3-protected hydroxymethyl-2-thiomethylcyclopentane derivative or the salt thereof is formed by stirring a (2S, 3R)-2-acyloxymethyl-3-protected hydroxymethylcyclopentanone represented by the following general formula (XIII)

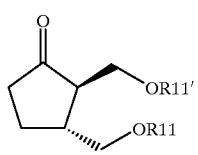

(XIII)

(wherein $R_{11}$ is the protective group of a hydroxy group and $R_{11}'$ is an acyl group of 1 through 10 carbon atoms and they may be identical with or different from each other) and a mercapto compound represented by the general formula (XIV)

$$HS—R_{10} \quad (XIV)$$

(wherein $R_{10}$ has the same meaning as defined above) in an inert solvent such as, for example, water, an alcohol type solvent like methanol, ethanol, or propanol, a water-soluble solvent like acetone, tetrahydrofuran, or dimethyl formamide, or a mixed solvent thereof, preferably in a water-acetone mixed solvent in the presence of a base such as an alkali hydroxide like sodium hydroxide, potassium hydroxide or lithium hydroxide or an alkali carbonate like potassium carbonate or sodium carbonate, preferably adding one equivalent weight of sodium hydroxide under mild conditions such as, for example, at a temperature in the range of from 0° C. the boiling point of the solvent, preferably between 0° C. to 50° C. The compound represented by the general formula (XI) is isolated by concentrating the resultant reaction solution and subsequently purifying the resultant concentrate by chromatography with Sephadex or silica gel or the like.

As examples of the (2S, 3R)-2-acyloxymethyl-3-protected hydroxymethylcyclopentanone represented by the general formula (XIII), the following compounds may be cited:

(2S,3R)-2,3-bis(acetoxymethyl) cyclopentanone,
(2S,3R)-2,3-bis(propionyloxymethyl) cyclopentanone,
(2S, 3R)-2,3-bis(benzyloxycarbonyloxymethyl) cyclopentanone.

As examples of the mercapto compound represented by the general formula (XIV), the following compounds may be cited:

Propyl mercaptan, alpha-thioglycerin, mercapto ethanol, 2-amino-ethyl mercaptan, and 2-carboxyethyl mercaptan.

As examples of the (2S, 3R)-3-protected hydroxymethyl-2-thiomethyl cyclopentanone derivative represented by the general formula (XI) mentioned above, the following cyclopentanone derivatives may be cited.

1. (2S, 3R)-3-Acetoxymethyl-2-[(2RS)-2,3-dihydroxypropyl-thiomethyl]cyclopentanone
2. (2S, 3R)-3-Acetoxymethyl-2-[(2-acetylamino) ethylthiomethyl]cyclopentanone
3. (2S, 3R)-3-Acetoxymethyl-2-[(2R)-(2-acetylamino-2-carboxy ethyl)thiomethyl]cyclopentanone
4. (2S, 3R)-3-Acetoxymethyl-2-[(2-hydroxyethyl) thiomethyl]cyclopentanone
5. (2S, 3R)-3-Acetoxymethyl-2-[(2-carboxyethyl) thiomethyl]cyclopentanone The method for synthesizing a (1R, 2S)-2-[(2R)-(2-protected or unprotected amino-2-carboxy) ethylthio] methyl-3-oxo-1-cyclopentane carboxylic acid (cystacyclin when the protective group of the amino group is acetyl group) or a pharmacologically acceptable salt thereof from a (2S, 3R)-3-protected hydroxymethyl-2-thiomethylcyclopentanone derivative represented by the general formula (XI) will be described more specifically below.

The functional group of the (2S, 3R)-3-protected hydroxymethyl-2-thiomethylcyclopentanone derivative represented by the general formula(XI) mentioned above, is protected when necessary, and the protected hydroxymethyl group at the 3 position is selectively deprived of the protective group. The removal of the protective group can be effected by the conventional method according to the kind of the protective group. When the protective group is acyl group, for example, the hydrolysis with an acid or an alkali in such a water-soluble solvent as methanol or acetone. Then, the thiomethyl group at the 2 position is oxidized into a sulfoxide methyl group or sulfonyl methyl group to obtain a (2S, 3R)-3-hydroxymethyl-2-sulfoxide- or sulfonyl-methylcyclopentanone derivative or a salt thereof corresponding to the general formula (XI). The hydroxymethyl group of the (2S, 3R)-3-hydroxymethyl-2-sulfoxide- or sulfonyl-methylcyclopentanone derivative is oxidized into a carboxyl group by the conventional method in a suitable organic solvent as, for example, by the chromic acid oxidation using a Jones reagent etc. in acetone solvent or by the ruthenium oxidation in a mixed solvent consisting of carbon tetrachloride, acetonitrile and water in the presence of sodium metaperiodate (NaIO$_4$) to obtain a (2S, 3R)-3-carboxy-2-sulfoxide- or sulfonyl-methylcyclopentanone derivatives represented by the general formula (XII) mentioned above.

Then, the derivative is caused to react with an N-protected-L-cysteine and optionally deprived of the protective group to obtain the (1R, 2S)-2-[((2R)-2-protected or unprotected amino-2-carboxy) ethylthio]-methyl-3-oxo-1-cyclopentanecarboxylic acid or the pharmaceutically acceptable salt thereof as aimed at.

As the protective group of the amino group, any of the acyl groups etc. which are in popular use can be used.

Specifically, the cystacyclin is synthesized as shown by the following flowsheet.

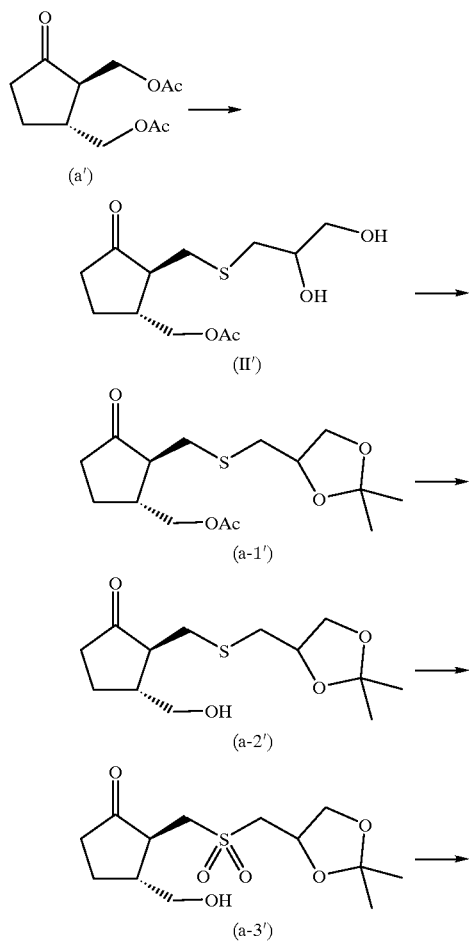

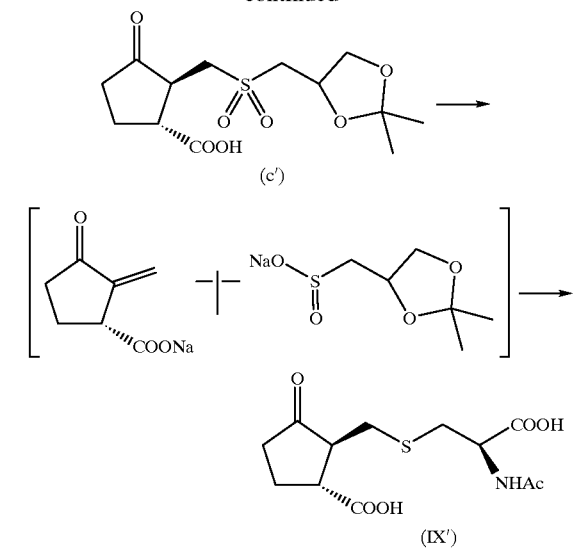

When the compound of the present invention is to be used as neuron differentiation accelerator, it is administered in the form of injections, oral preparations, suppositories, etc., either alone or as a mixture thereof with pharmaceutical additives such as excipient(s) or carrier(s). Any of the pharmaceutical additives which are pharmaceutically acceptable ones and which are usually used can be used and proper additives are determined depending on the administration route and the administration method etc. As a liquid carrier, for example, used maybe water, alcohols, animal and vegetable oils and synthetic oils. As a solid carrier, used may be, for example, saccharide such as monosaccharide, oligosaccharide or polysaccharide.

In the case of injection, it is generally desirable to use physiological salt solution, various buffers, solutions of sugars such as glucose, inositol and mannitol etc. or glycols such as ethylene glycol, propylene glycol and polyethylene glycol.

It may be also possible that the compound of the present invention is dissolved, prior to the administration, in a appropriate solvent for injection (for example, a liquid for intravenous administration such as sterilized water, physiological salt solution, a glucose solution, an electrolyte solution or an amino acid solution) together with an excipient such as a sugar, for example, inositol, mannitol, glucose, mannose, maltose or sucrose, or an amino acid, for example phenylalanine.

The content of this compound in the pharmaceuticals is usually in the range from 0.1 to 100% by weight, preferably from 1 to 98% by weight, though it varies depending on the pharmaceuticals. In the case of an injection, for example, the content of the active ingredient is usually in the range from 0.1 to 30% by weight, preferably from 1 to 10% by weight. When orally administered, the compound is formulated together with the above-mentioned solid or liquid carrier(s) into tablets, capsules, powders etc. The composition generally contains the active ingredient in the range from 5 to 100% by weight, preferably from 25 to 98% by weight.

The dose may be determined depending on the age, body weight and conditions of the patient, the purpose of the treatment, etc. The therapeutic dose is generally in the range of from 1 to 200 mg/kg. day when parenterally administered, and from 2 to 500 mg/kg. day when orally administered.

All the compounds of the present invention are characterized by having a low toxicity and showing only a small accumulated toxicity when continuously administered. When intraperitoneally administered at once to a mouse in a dose of 500 mg/kg, the compound of the present invention shows no symptom of toxicity.

Now, the physiological activity of 2,3-di-substituted cyclopentanone derivatives of the general formula (I) of this invention will be shown below by a test example.

TEST EXAMPLE

Activity of the Compound of the Present Invention to Elongate Neuroid Apophysises of PC 12 cells The compound of the present invention was assayed by morphological change in accordance with the method of Green et al. [Ann. REV. Neurosi., Vol. 3, page 353 (1980)].

In a Dulbecco modified Eagle culture medium, incorporating 10% of bovine fetal serum and 10% equine serum therein, PC 12 cells were inoculated at a rate of 10000 cells/ml and cultured overnight with a collagen coat 96-hole multiplate under the conditions of 37° C. and 5% $CO_2$. A sample compound was added to the cultured broth and left standing therein for one day. At the end of the standing, the cultured broth was microscopically observed to examine morphological change.

As a result, the minimum effective doses (MED, ug/ml) with which each of the compounds induced elongation of neuroid processes of the PC 12 cells were found as the following Table 2 shows.

TABLE 2

Minimum effective dose to induce elongation neuroid apophysises of PC 12 cells

| Compound No. | MED (ug/ml) |
|---|---|
| I | 0.39 |
| II | 0.39 |
| III | 0.78 |
| IV | 0.39 |
| V | 0.78 |
| VI | 0.20 |
| VII | 1.56 |
| VIII | 1.56 |
| IX | 3.13 |
| X | 0.39 |
| XI | 0.39 |
| XII | 1.56 |
| XIII | 0.78 |

EXAMPLES

The following examples to describe the present invention specifically are not intended to limit the scope of this invention.

Example 1

Production of trans-3-acetoxymethyl-2-[(2,3-dihydroxypropyl)thiomethyl]cyclopentanone [Compound (I)]

(1) Production of trans-2,3-bis(acetoxymethyl)-cyclopentanone [Compound (a)]

Trans-2,3-bis(hydroxymethyl)-cyclopentanone (3.70 g, 25.7 mmols) was dissolved in anhydrous pyridine (20 ml), and added acetic anhydride (20 ml) at cool. And it was stirred at room temperature for four hours. The reaction solution was concentrated under a reduced pressure. The residue was added water (100 ml) and extracted three times with ethyl acetate (70 ml). The ethyl acetate layer was washed with saturated sodium chloride solution (100 ml) and dried over anhydrous sodium sulfate, and concentrated under a reduced pressure to obtain a residue. The residue was purified by silica gel column chromatography (250 ml, chloroform:methanol=50:1) to obtain the compound (a) (4.89 g, 21.4 mmol, yield 83.4%).

$^1$H-NMR (200 MHz, CDCl$_3$); δ: 1.56–1.78 (1H, m), 2.03 (3H,m), 2.08 (3H, s), 2.04–2.31 (3H, m), 2.35–2.55 (2H, m), 4.14–4.26 (2H, m), 4.27–4.43 (2H, m); MS (FAB, POS) m/z: 229 (M+H)$^+$

The raw material,trans-2,3-bis(hydroxymethyl)-cyclopentanone, was obtained by firstly protecting the ketone moiety of trans-2,3-bis(methoxycarbonyl)-cyclopentanone [W. L. White, P. B. Anzeveno and F. Tohnson, J. Org. Chem., 47, 2379 (1982)], and then reducing to hydromethyl group by the general method, and removing the protecting group of ketone.

The method for protection of the ketone moiety is, for example, to convert the ketone moiety to ketal with 2 equivalent of methyl orthoformate in the presence of 0.05 equivalent of p-toluenesulphonic acid in methanol. Further also, the method for the reduction to hydromethyl group is, for example, to reduce with 2 equivalent of lithium aluminum hydride in anhydrous ether under ice cooling. The protecting group of ketone moiety may be removed with hydrochloric acid in acetone at room temperature.

(2) Production of trans-3-acetoxymethyl-2-[(2,3-dihydroxy-propyl)thiomethyl]cyclopentanone [Compound (I)]

A solution of trans-2,3-bis(acetoxymethyl)-cyclopentanone [Compound (a)](18.72 g, 81.8 mmols] in acetone (160 ml)was added to alphathioglycerin (8.7 g, 81.8 mmols), and stirred at room temperature for 20 minutes. The reaction solution was concentrated under a reduced pressure to obtain a residue. The residue was dissolved in methanol and added silica gel (100 g), and then dried under the reduced pressure. The dry residue was purified with silica gel column chromatography (300 ml, dichloromethane methanol=20:1, 5:1) to obtain the target compound (I) (21.88 g, 79.27 mmol, yield 96.8%).

$^1$H-NMR (200 MHz, CD$_3$OD) δ: 1.56–1.79 (1H, m), 2.07 (3H,s), 2.10–2.96 (9H, m), 3.56–3.60 (2H, m), 3.66–3.78 (1H, m), 4.21–4.34 (2H, m); MS (FAB, POS) m/z: 277 (M+H)$^+$

Example 2

Production of Compound (I) by Another Method.

(1) Production of Trans-3-(acetoxy)methyl-2-methylene-cyclopentanone [Compound (b)]

Trans-2,3-bis(acetoxymethyl)-cyclopentanone [Compound (a)](2350 mg, 10.3 mmols) was dissolved in tetrahydrofuran (25 ml), added triethyl amine (2.87 ml) to the solution, and refluxed for one hour. The reaction solution was concentrated under a reduced pressure. Water (20 ml) was added to the solution, and extracted three times with ethyl acetate (20 ml). The ethyl acetate layer was washed with saturated sodium chloride solution (20 ml), dried over anhydrous sodium sulfate, and concentrated under a reduced pressure to obtain a residue. The residue was purified by silica gel column chromatography (40 ml, hexane : ethyl acetate=4:1) to obtain the compound (b) (1575 mg, 9.37 mmol, yield 91%).

$^1$H-NMR (60 MHz, CDCl$_3$) δ : 1.48–1.81 (1H, m), 2.10 (3H,s), 2.16–2.73 (3H, m), 2.73–3.40 (1H, m), 4.00–4.31 (2H,m), 5.34 (1H, d, J=3 Hz), 6.15 (1H, d, J=3 Hz); MS (FAB, POS) m/z: 169 (M+H)$^+$ (2) Production of the compound (I).

A solution of 3-acetoxymethyl-2-methylidene-cyclopentanone [Compound (b)] (1780 mg, 10.59 mmols) in acetone (50 ml) was added to alpha-thioglycerin (1122 mg, 10.59 mmols), stirred overnight at room temperature. The reaction solution was concentrated. The residue was purified by Sephadex LH-20 (300 ml, methanol) to obtain the compound (I) (1569 mg, 5.68 mmol, yield 53.6%).

Example 3

Production of trans-3-acetoxymethyl-2-[(2-acetyl-amino-2-carboxy-ethyl)thiomethyl]-cyclopentanone [Compound (II)]

A solution of trans-2,3-bis(acetoxymethyl)-cyclopentanone [Compound (a)] (205 mg, 0.899 mmol) in acetone (7.2 ml) was added to N-acetyl-L-cysteine (147 mg, 0.899 mmol), and then added IN-sodium hydroxide (1.8 ml), stirred at room temperature for 15 minutes. The reaction solution was concentrated. The residue was purified by Sephadex LH-20 (11.80% aqueous methanol) to obtain the compound (II) (276 mg, yield 86.9%).

$^1$H-NMR (200 MHz, $D_2O$); δ: 1.50–1.80(1H,m), 1.59–2.60(5H, m), 2.00(3H,s), 2.07(3H, s), 2.73–3.10(4H, m), 4.16–4.28 (2H, m), 4.29–4.38 (1H, m); MS (FAB, NEG) m/z: 331 (M–H)$^-$

Example 4

Production of trans-3-acetoxymethyl-2-[(2-acetyl-amino-ethyl)thiomethyl]cyclopentanone [Compound (IV)].

Trans-2,3-bis(acetoxymethyl)-cyclopentanone [Compound (a)] (205 mg, 0.898 mmol) was dissolved in acetone (7.2 ml), added N-acetyl-L-cysteamine (113 mg, 0.948 mmol) and 1N-sodium hydroxide (0.9 ml), and then stirred at room temperature for one hour. The reaction solution was concentrated. The residue was purified by Sephadex LH20 (11.80% aqueous methanol) to obtain the target compound (IV) (250 mg, yield 98.0%).

$^1$H-NMR (200 MHz, $CDCl_3$); δ: 1.51–1.81 (1H, m), 2.00 (3H,s), 2.09 (3H, s), 2.05–2.31 (3H, m), 2.32–2.60 (2H, m), 2.61–2.75 (2H, m), 2.78–3.05 (2H, m), 3.38–3.62 (2H, m), 4.08–4.35 (2H, m); MS (FAB, POS) m/z: 288 (M+H)$^+$

Example 5

Production of trans-2-[(2-acetylamino-2-carboxy-ethyl) thiomethyl]-3-hydroxymethyl-cyclopentanone [Compound (III)]

Trans-3-acetoxymethyl-2-[(2-acetylamino-2-carboxy-ethyl)-thiomethyl]-cyclopentanone [Compound (II)] (24 mg, 0.072 mmol) was dissolved in methanol (0.6 ml), added 1N-sodium hydroxide under ice cooling, and then stirred for three hours. The reaction solution was adjusted to pH 7.0 with 1N-hydrochloric acid, and added silica gel (100 mg) thereto, concentrated to dryness. The residue was purified by silica gel column chromatography (15 ml, butanol:acetic acid : water=10:1:1) to obtain the compound (III) (14.7 mg, yield 69.4%).

$^1$H-NMR (200 MHz, $D_2O$); δ: 1.55–1.81 (1H, m), 2.08 (3H,s), 2.08–2.61 (5H, m), 2.85–3.18 (4H, m), 3.58–3.90 (2H,m), 4.56–4.69 (1H, m)

Example 6

Production of trans-3-acetoxymethyl-2-[(2-hydroxy-ethyl) thiomethyl]-cyclopentanone [Compound (V)].

Trans-3-acetoxymethyl-2-methylidene-cyclopentanone [Compound(b)] (31 mg, 0.184 mmol) was added acetone (1 ml), methanol (1 ml) and mercapto ethanol (0.018 ml), stirred at room temperature for one hour. The reaction solution was concentrated. The residue was purified by silica gel column chromatography (20 ml, hexane:ethyl acetate =1:2) to obtain the compound (V) (22 mg, 0.089 mmol, yield 48.6%).

$^1$H-NMR (60 MHz, $CDCl_3$); δ: 1.40–1.98 (1H, m), 1.98 (3H,s), 2.02–2.51 (5H, m), 2.52–2.95 (4H, m), 3.67 (2H, m), 4.01–4.18 (2H, m)

Example 7

Production of trans-3-hydroxymethyl-2-[(3-methoxy-carbonyl-pyridin-2-yl)thiomethyl]cyclopentanone [Compound (VI)].

3-acetoxymethyl-2-methylidene-cyclopentanone [Compound(b)] (60 mg, 0.357 mmol) was dissolved in acetone (1 ml), added a solution of 3-methoxycarbonyl-2-mercaptopyridine (60 mg, 0.357 mmol) in methanol (2 ml), and then stirred at room temperature for 15 hours. The reaction solution was concentrated. The residue was purified by silica gel column chromatography (20 ml, hexane:ethyl acetate=2:1) to obtain the condensate (85 mg, yield 70.8%). The obtained condensate (5 mg) was dissolved in methanol (1.5 ml), added concentrated-hydrochloric acid (0.5 ml), and then stirred at room temperature for two hours. The reaction solution was concentrated. The residue was purified by silica gel column chromatography (20 ml, dichloromethane :methanol=20:1) to obtain the compound (VI) (9.3 mg, yield 70.8%).

$^1$H-NMR (60 MHz, $CDCl_3$); δ: 1.52–2.20 (1H, m), 2.18–2.70 (5H, m), 3.33–3.66 (3H, m), 3.70–4.10 (1H, m), 3.91 (3H, s), 7.08 (1H, dd, J=5.0 Hz, 8.0 Hz), 8.20 (1H, dd, J=2.1 Hz, 8.0 Hz), 8.54 (1H, dd, J=2.1 Hz, 8.0 Hz)

Example 8

Production of trans-2-[(2-acetylamino-2-methoxy-carbonyl-ethyl)thiomethyl]-3-oxo-1-cyclopentanecarboxylic acid [Compound (VII)].

(1) Production of trans-3-acetoxymethyl-2-[(2,3-isopropylidenedioxy-propyl)thiomethyl]cyclopentanone [Compound (a-1)]

Trans-3-acetoxymethyl-2-[(2,3-dihydroxypropyl) thiomethyl]-cyclopentanone [Compound (I)] (21.9 g, 79.27 mmols) was dissolved in anhydrous acetone (120 ml), added p-toluene sulfonic acid (1.4 g) and dimethoxy propane (29.4 ml) under ice cooling, and then stirred at room temperature for 30 minutes. The reaction solution was added water (140 ml) and ethyl acetate (280 ml). The aqueous layer was adjusted to pH 7.0 with saturated sodium carbonate, and then extracted twice with ethyl acetate (280 ml). The ethyl acetate layer was washed with saturated sodium chloride solution (150 ml), dried over anhydrous sodium sulfate, and then concentrated under a reduced pressure to obtain the compound (a-1) (23.34 g, 73,87 mmols, yield 93.2%).

$^1$H-NMR (200 MHz, $CDCl_3$); δ: 1.35 (3H, s), 1.42 (3H, s), 1.50–1.76 (1H, m), 2.08 (3H, m), 2.10–2.96 (9H, m), 3.65–3.74 (1H, m), 4.05–4.18 (2H, m), 4.18–4.29 (2H, m); MS (FAB, POS) m/z: 317 (M+H)$^+$ (2) Production of trans-3-hydroxymethyl-2-[(2,3-isopropylidenedioxypropyl)thiomethyl]cyclopentanone [Compound (a-2)].

Trans-3-acetoxymethyl-2-[(2,3-isopropylidenedioxypropyl)-thiomethyl]cyclopentanone [Compound (a-1)] (1097 mg, 3.47 mmols) obtained in above-described (1) was dissolved in methanol (20 ml), added 1N-sodium hydroxide solution (3.47 ml) under ice cooling, and then stirred at room temperature for 15 minutes. The solution was adjusted to pH 7.0 with 1N-hydrochloric acid under ice cooling, and then concentrated under a reduced pressure to obtain a resedue. Water(3 ml) was added to the residue, and extracted three times with ethyl acetate (15 ml). The ethyl acetate layer was washed with saturated sodium chloride solution (10 ml), dried over anhydrous sodium sulfate, and concentrated under a reduced pressure to obtain a resedue. The residue was purified by silica gel column chromatography (50 ml, chloroform:methanol= 30:1) to obtain the compound (a-2) (739 mg, 2.69 mmols, yield 77.5%).

¹H-NMR (200 MHz, CDCl₃); δ: 1.35 (3H, s), 1.43 (3H, s), 1.58–1.81 (1H, m), 2.00–2.81 (9H, m), 3.02–3.11 (1H, dd, J=3.5, 13.2 Hz), 3.64–3.73 (1H, m), 3.76–3.91 (2H, m), 4.06–4.34 (2H, m); MS (FAB, POS) m/z: 275 (M+H)⁺

(3) Production of trans-3-hydroxymethyl-2-[(2,3-isopropylidenedioxypropyl)sulfonylmethyl]cyclopentanone [Compound (a-3)].

Trans-3-hydroxymethyl-2-[(2,3-isopropylidenedioxypropyl)thio-methyl]cyclopentanone [Compound (a-2)] (5140 mg, 18.76 mmols) obtained in above-described (2) was dissolved in dichloromethane(50 ml), added m-chloroperbenzoic acid (80% in purity, 8093 mg, 37.32 mmols) in dichloromethane (80 ml) under ice cooling, and then stirred at room temperature for two hours. The reaction solution was filtered. The filtrate was added 20% sodium hydrogen sulfite solution (6 ml), saturated sodium carbonate solution (6 ml) and water (50 ml), and stirred, and then separated the dichloromethane layer. The dichloromethane layer was washed with saturated sodium chloride solution (30 ml), dried over anhydrous sodium sulfate, and then concentrated under a reduced pressure to obtain a residue. The residue was separated by silica gel column chromatography (160 ml, hexane:ethyl acetate=1:3) to obtain the compound (a-3) (4610 mg, 15.06 mmol, yield 80.3%).

¹H-NMR (200 MHz, CDCl₃); δ: 1.37 (3H, s), 1.46 (3H, s), 1.73–1.92 (1H, m), 1.98–2.73 (6H, m), 3.10–3.49 (3H, m), 3.68–4.08 (4H, m), 4.16–4.24 (1H, dd, J=6.14. 7.42 Hz), 4.56–4.68 (1H, m); MS (FAB, POS) m/z: 307 (M+H)⁺

(4) Production of trans-2-[(2,3-isopropylidenedioxypropyl) sulfonylmethyl]-3-oxo-1-cyclopentanecarboxylic acid [Compound (c)].

Trans-3-hydroxymethyl-2-[(2,3-isopropylidenedioxypropyl) sulfonylmethyl] cyclopentanone [Compound (a-3)] (2630 mg, 8.59mmol) obtained in above-described (3) was dissolved in acetone (150 ml),added Jones reagent until the color of the solution turned orange. And 2-propanol was added to the reaction solution until the color turned green under ice cooling. The solution was concentrated under a reduced pressure. Water (60 ml) was added to the residue, extracted three times with dichloromethane (100 ml). The dichloromethane layer was washed with saturated sodium chloride solution (40 ml), thereafter dried over anhydrous sodium sulfate, and concentrated under a reduced pressure to obtain the compound (c) (1948 mg, 6.08 mmols, yield 70.8%). This product was used in the next step without further purification.

¹H-NMR (200 MHz, CDCl₃); δ: 1.37 (3H, s), 1.43 (1.5H, s), 1.47 (1.5H, s), 2.02 (1H, m), 2.22–2.65 (3H, m), 2.94–3.32 (3H, m), 3.32–3.84 (4H, m), 4.19 (1H, m), 4.40 (1H, brs), 4.59 (1H, m); MS (ESI, NEG) m/z: 319 (M–H)⁻

(5) Production of trans-2-[(2-acetylamino-2-methoxycarbonyl-ethyl)thiomethyl]-3-oxo-1-cyclopentanecarboxylic acid [Compound (VII)].

Trans-2-[(2,3-isopropylidenedioxypropyl) sulfonylmethyl) -3-oxo-1-cyclopentanecarboxylic acid [Compound (c)] (261 mg,0.81 mmol) obtained in above-described (4) and N-acetyl-L-cysteine methyl ester (144.5 mg, 0.81 mmol) were dissolved in acetone (8 ml) and methanol (2 ml), and added 1N-sodium hydroxide (1.62 ml) and water (4 ml), and then stirred at room temperature for one hour and half. The solution was concentrated. Water (3 ml) was added to the residue, and adjusted to pH 2.0 with 1N hydrochloric acid, and then extracted three times with dichloromethane (4 ml). The dichloromethane layer was washed with saturated sodium chloride solution (5 ml), then dried over sodium sulfate, and concentrated to dryness to obtain a residue. This residue was purified by silica gel column chromatography (80 ml,dichloromethane:methanol=20:1) to obtain the target compound. This compound was dissolved in methanol (10 ml) and water (3 ml), adjusted to pH 6.8 with 1N-sodium hydroxide, and then concentrated to dryness to obtain the sodium salt of the compound (VII) (208.2 mg, yield 75.8%).

¹H-NMR (200 MHz, D₂O); δ: 1.75–1.95 (1H, m), 2.00 (3H, s), 2.05–2.60 (3H, m), 2.65–3.25 (6H, m), 3.72 (3H, s), 4.52–4.66 (1H, m) MS (FAB, NEG) m/z: 316 (m–H)⁻

Example 9

Production of trans-2-[(2-acetylamino-2-allyloxycarbonyl-ethyl)thiomethyl]-3-oxo-1-cyclopentanecarboxylic acid Compound(VIII)].

Trans-2-[(2,3-isopropylidenedioxypropyl) sulfonylmethyl]-3-oxo-1-cyclopentane carboxylic acid [Compound (c)] (228.6 mg, 0.714mmol) and N-acetyl-L-cysteine allyl ester (145 mg, 0.714 mmol) were dissolved in acetone (5 ml), added 1N-sodium hydroxide (1.42 ml), stirred at room temperature for one hour. The reaction solution was concentrated. Water (3 ml) was added thereto, then adjusted to pH 2.5 with 1N hydrochloric acid, and extracted three times with ethyl acetate (3 ml). The ethyl acetate layer was washed with saturated sodium chloride solution (5 ml), and then dried over sodium sulfate to dryness and concentrated to obtain a residue. This residue was purified by silica gel column chromatography (50 ml, dichloromethane:methanol=20:1) to obtain the compound (VIII) (95 mg, yield 38.4%).

¹H-NMR (200 MHz, CDCl₃); δ: 1.93–2.18 (1H, m), 2.08 (1.5H, s), 2.11 (1.5H, s), 2.20–2.68 (3H, m), 2.69–3.18 (6H, m), 4.63–4.69 (2H, m), 4.80–4.94 (1H, m), 5.23–5.44 (2H, m), 5.81–6.04 (1H, m), 6.78 (0.5H, d, J=6.9 Hz), 6.90 (0.5H, d, J=6.9 Hz), 9.00 (1H, brs); MS (ESI, NEG) m/z; 342 (M–H)⁻

Example 10

Production of trans-2-[(2-acetylamino-2-carboxy-ethyl) thiomethyl]-3-oxo-1-cyclopentanecarboxylic acid [Compound (IX)].

A solution (51 ml) of trans-2-[(2,3-isopropylidenedioxy-propyl)sulfonylmethyl]-3-oxo-1-cyclopentanecarboxylic acid [Compound (c)] (1366 mg, 4.268 mmols) in acetone was added to a solution of N-acetyl-L-cysteine (695 mg, 4.268 mmols) in 1N-sodium hydroxide (12.8 ml), stirred at room temperature for two hours. The reaction solution was concentrated, and then purified with a Sephadex LH-20 (11.80% aqueous methanol) to obtain the disodium salt of the target compound (IX) (1185 mg, yield 80.0%).

¹H-NMR (200 MHz, D₂O); δ: 1.74–1.95 (1H, m), 2.00 (3H, s), 2.06–2.61 (3H, m), 2.62–3.07 (6H, m), 4.30 (1H, m); MS (FAB, NEG) m/z: 302 (M–H)⁻

Example 11

Production of trans-2-[(2-acetylamino-2-carboxyl-ethyl) thiomethyl]-3-methoxycarbonyl cyclopentanone [Compound (X)].

(1) Production of trans-2-[2,3-isopropylidenedioxypropyl-sulfonylmethyl]-3-methoxycarbonyl cyclopentanone[Compound (d)].

Trans-2-[(2,3-isopropylidenedioxypropyl) sulfonylmethyl]-3-oxo-1-cyclopentanecarboxylic acid [Compound (c)] (160 mg,0.5 mmol) was dissolved in methanol (15 ml), added an ether solution of diazo-methane until the reaction solution turned yellow. Thereafter, the solution was concentrated under a reduced pressure to obtain a solution. The residue was purified by silica gel column chromatography (15 ml, hexane:ethyl acetate=1:2) to obtain the compound (d) (148 mg, 0.443 mmol, yield 88.6%).

$^1$H-NMR (200 MHz, CDCl$_3$); δ: 1.37 (3H, s), 1.43 (1.5H, s), 1.46 (1.5H, s), 1.90–2.09 (1H, m), 2.20–2.65 (3H, m), 2.90–3.24 (3H, m), 3.27–3.89 (4H, m), 3.77 (3H, s), 4.18 (1H, m), 4.57 (1H, m).

(2) Production of trans-2-[(2-acetylamino-2-carboxyl-ethyl)thiomethyl]-3-methoxycarbonyl-cyclopentanone [Compound (X)].

Trans-2-[(2,3-isopropylidenedioxypropyl)sulfonylmethyl]-3-methoxycarbonyl cyclopentanone [Compound (d)] (64 mg, 0.91mmol) was dissolved in acetone (2 ml), added N-acetyl-L-cysteine (31.2 mg, 0.191 mmol) dissolved in 1N-sodium hydroxide (0.191 ml), and then stirred at room temperature for one hour. The solution was concentrated, and then purified with Sephadex LH-20 (250 ml, 80% aqueous methanol) to obtain the sodium salt of the compound (X) (60 mg, yield 92.1%).

$^1$H-NMR (200 MHz, D$_2$O); δ: 1.82–2.06 (1H, m), 1.86 (3H, s), 2.00 (3H, s), 2.16–2.58 (3H, m), 2.62–3.20 (6H, m), 3.72 (3H, s), 4.30 (1H, m); MS (ESI, NEG) m/z: 316 (M–H)$^-$

Example 12

Production of trans-2-(2-acetylaminoethyl) thiomethyl]-3-methoxycarbonyl-cyclopentanone [Compound (XI)].

By using N-acetylamino-ethyl mercaptan in the place of the N-acetyl-L-cysteine in the example 11, the compound (XI) was obtained by the same manner as that of Example 11.

$^1$H-NMR (200 MHz, CDCl$_3$); δ: 1.89–2.08 (1H, m), 2.00 (3H, s), 2.09–2.43 (3H, m), 2.45–2.83 (4H, m), 2.88–3.12 (2H, m), 3.36–3.49 (2H, m), 3.78 (3H, s), 6.15 (1H, brs); MS (FAB, POS) m/z: 274 (M+H)$^+$ Example 13

Production of trans-2-[(2-acetylaminoethyl)-thiomethyl]-3-oxo-1-cyclopentane carboxylic acid [Compound (XII)].

Trans-2-[(2-acetylamino)ethylthio]methyl-3-methoxycarbonyl-cyclopentanone [Compound (XI)] (60 mg, 0.219 mmol) was dissolved in methanol (3 ml), added 3N hydrochloric acid (2 ml), stirred at room temperature for eight hours and then stirred at 10° C. for 15 hours. The reaction solution was adjusted to pH 7.0 with 1N sodium hydroxide, and concentrated until drying. The residue was purified by silica gel column chromatography (20 ml, dichloromethane:methanol=10:1) to obtain the compound (XII) (20 mg).

$^1$H-NMR (200 MHz, CD$_3$OD); δ: 1.86–2.10 (1H, m), 1.94 (3H, s), 2.10–2.52 (3H, m), 2.60–3.18 (2H, m), 3.28–3.37 (2H, m); MS (FAB, NEG) m/z: 258 (M–H)$^-$

Example 14

Production of trans-2-[(2,3-dihydroxypropyl)oxy methyl]-3-hydroxymethyl cyclopentanone [Compound (XIII)].

(1) Productionof trans-2,3-bis(acetoxymethyl)-1,1-ethylene-dioxy-cyclopentane [Compound(a-4)] and trans-2,3-bis(hydroxymethyl)-1,1-ethylenedioxy- cyclopentane [Compound (a-5)].

Trans-2,3-bis(acetoxymethyl)-cyclopentanone [Compound(a)] (4980 mg, 21.4 mmols) was dissolved in anhydrous benzene (30 ml), added pyridium-p-toluenesulfonic acid (1062 mg) and ethylene glycol (2.8 ml, 42.8 mmols), and refluxed with a water separating unit attached to the reflux condenser.

The reaction solution was concentrated. Thereafter water (30 ml) was added to the residue, extracted three times with ethyl acetate(40 ml). The ethyl acetate layer was washed with saturated sodium chloride solution (30 ml), then dried over sodium sulfate, and concentrated to dries to obtain a crude compound (a-4) (5200 mg). This crude compound was dissolved in methanol (60 ml), added 1N sodium hydroxide (43 ml) stirred for 10 minutes, and then neutralized with 0.1N hydrochloric acid. The resultant solution which was added silica gel (15 g) were concentrated to dryness. The residue was purified by silica gel column chromatography (200 ml, chloroform methanol=20:1) to obtain the compound (a-5) (2902 mg).

$^1$H-NMR (200 MHz, CD$_3$OD); δ: 1.20–1.43 (1H, m), 1.68–2.22 (5H, m), 3.38–3.80 (6H, m), 3.85–4.03 (4H, m)

(2) Production of the mixture of trans-3-(t-butyldimethyl-silyloxy-methyl)-1,1-ethylenedioxy-2-hydroxymethyl-cyclopentane [Compound (a-6-1)] and trans-2-(t-butyl-dimethylsilyloxymethyl)-1,1-ethylenedioxy-3-hydroxymethyl-cyclopentane [Compound (a-6-2)]; trans-2-acetoxymethyl-3-(t-butyldimethylsilyloxymethyl)-1,1-ethylene-dioxy-cyclopentane [Compound (a-7-1)]; and trans-3-acetoxymethyl-2-(t-butyldimethylsilyloxy-methyl)-1,1-ethylenedioxy-cyclopentanone [Compound (a-7-2)].

The compound (a-5) (4300 mg, 24.15 mmols) obtained by the method of the above (1) was dissolved in dimethyl formamide (5 ml), added imidazole (3641 mg, 50.7 mmol) and t-butyldimethylsilyl chloride (3641 mg, 24.15 mmols), and stirred at room temperature for two hours. The reaction solution was concentrated to dryness. Water (100 ml) was added to the residue, and extracted twice with dichloromethane (200 ml). The dichloromethane layer was washed with saturated sodium chloride solution (100 ml), then dried over sodium sulfate, and concentrated to obtain a residue. This residue was purified by silica gel column chromatography (230 ml, hexane:ethyl acetate=3:1)to obtain the mixture of the compound (a-6-1) and the compound (a-6-2) (3450 mg).

This mixture was dissolved in dichloromethane (50 ml), added dimethylaminopyridine (144 mg), acetic anhydride (1.33 ml) and pyridine (1.97 ml) under ice cooling, stirred at room temperature for two hours. The reaction solution was concentrated. Thereafter, the residue was purified by silica gel column chromatography (300 ml, hexane:ethyl acetate= 4:1–2:1) to obtain the compound (a-7-1) (2720 mg, 8.14 mmols) and the compound (a-7-2) (884 mg, 3.02 mmols).

TLC (Rf, hexane:ethyl acetate 4:1); Compound(a-7-1)= 0.47, Compound(a-7-2)=0.56;

$^1$H-NMR [(a-7-1), 200 MHz, CDCl$_3$); δ: 0.04 (6H, s), 0.88 (9H, s), 1.38–1.51 (1H, m), 1.69–2.18 (5H, m), 2.03 (3H, s), 3.59 (2H, m), 3.89 (4H, m), 4.08–4.22 (2H, m)

(3) Isolation of compound (a-6-1) and production of trans-3-(t-butyldimethylsilyloxymethyl)-1,1-ethylenedioxy-2-mesyloxymethyl)-cyclopentane [Compound (e)].

The compound (a-7-1) obtained by the process described above (2) (2780 mg, 8.14 mmols) was dissolved in methanol (30 ml), added 1N-Sodium hydroxide (8.14 ml), stirred for 15 minutes. The reaction solution was neutralized with 1N hydrochloric acid under ice cooling, and then concentrated. Water (50 ml) was added to the residue, extracted twice with dichloromethane (100 ml). The dichloromethane layer was washed with saturated sodium chloride solution (50 ml), then dried over sodium sulfate, and concentrated to dryness to obtain a crude compound (a-6-1,2130 mg, yield 89.6%).

The compound (a-6-1, 278 mg, 0.95 mmol) was dissolved in pyridine (3 ml) under ice cooling, added mesyl chloride (80 μl, 0.53 mmol), and stirred for one hour. The reaction solution was concentrated, then water (20 ml) was added, and extracted twice with dichloromethane (20 ml). The dichloromethane layer was washed with saturated sodium chloride solution (10 ml), then dried over sodium sulfate, and concentrated to obtain a residue. The residue was purified by silica gel column chromatography (20 ml, dichloromethane:methanol=60:1) to obtain the compound (e) (351 mg, yield 99.85%).

$^1$H-NMR (60 MHz, CDCl$_3$); δ: 0.03 (6H, s), 0.19 (9H, s), 1.32–2.35 (5H, m), 2.98 (3H, s), 3.59 (2H, m), 3.75–3.89 (4H, m), 4.30 (2H, m)

(4) Production of trans-2-[(2,3-dihydroxypropyloxy) methyl]-3-hydroxymethyl-cyclopentanone [Compound (XIII)].

Trans-2,2-dimethyl-1,3-dioxolan-4-yl-methanol (65.6 mg, 0.497 mmol) was dissolved in anhydrous benzene (15 ml), added sodium hydride (60% in purity, 49.7 mg), stood at room temperature for 30 minutes and then heated at 50° C. for 10 minutes. And the solution of 3-(t-butyldimethylsilyloxymethyl)-1,1-ethylenedioxy-2-(mesyloxymethyl)-cyclopentane [Compound (e)] (230 mg, 0.497 mmol) in anhydrous benzene (5 ml) was added thereto, and then heated and refluxed for eight hours. The reaction solution was cooled in an ice bath, added ethyl acetate (20 ml), ethanol (0.5 ml) and water (20 ml), and separated layers. Thereafter, aqueous layer was further extracted with ethyl acetate (20 ml). The ethyl acetate layer was washed with saturated sodium chloride solution (10 ml), then dried over sodium sulfate, and concentrated to obtain a residue. The residue was purified by silica gel column chromatography (75 ml, dichloromethane:methanol=40:1) to obtain the condensate therefrom (43 mg).

The condensate was dissolved in methanol (3 ml), added p-toluenesulfonic acid (10 mg), and stirred at room temperature for 15 hours. The reaction solution was concentrated. The residue was purified by silica gel column chromatography (20 ml, dichloromethane:methanol 20:1) to obtain the compound (XIII) (6.3 mg).

$^1$H-NMR (60 MHz CDCl$_3$); δ: 1.35–2.30 (4H, m), 3.30–4.80 (11H, m) MS (FAB, POS) m/z: 201 (M+H–H$_2$O)$^+$

Example 15

Production of trans-2-[(2-acetylamino-2-methoxy-carbonylethyl)thiomethyl)]-3-methoxycarbonyl-1-cyclopentanone [Compound XV].

3-Methoxycarbonyl-2-methylidene cyclopentanone [compound(g)] (3.0 mg, 0.0195 mmol) and N-acetyl-L-cysteine methyl ester (8.6 mg, 0.0487 mmol) were dissolved in acetonitrile (50 μl), added 2,2-azabis-isobutyronitrile (0.1 mg), and stirred at 80° C. for 24 hours. The reaction solution was concentrated. And then the residue was purified by silica gel column chromatography (10 ml, ethyl acetate) to obtain the target compound (4.0 mg, yield 61.9%).

$^1$H-NMR (200 MHz, CDCl$_3$); δ: 1.83–3.18 (10H, m), 2.06 (1.5H, s), 2.08 (1.5H, m), 3.76 (3H, s), 3.78 (3H, s), 4.78–4.90 (1H, m), 6.56–6.58 (1H,m) MS (FAB, POS) m/z: 332 (M+H)$^+$

Example 16

Production of disodium salt of trans-2-[(2-acetyl-amino-2-carboxy-ethyl)thiomethyl]-3-oxo-1-cyclopentane carboxylic acid [Compound (IX)].

(1) Trans-2-[(2-acetylamino-2-methoxycarbonylethyl)-thiomethyl]-3-methoxycarbonyl-1-cyclopentanone [Compound (XV)] (4 mg, 0.012 mmol) and 3N hydrochloric acid (1 ml) were added thereto, stirred at room temperature for 18 hours. The reaction solution was neutralized with 1N-sodium hydroxide, and then concentrated to dryness. The residue was purified with Sephadex LH-20 (20 ml, 80% hydrated methanol) to obtain the target compound (IX) (1.8 mg, 0.0051 mmol, yield 43%).

$^1$H-NMR (200 MHz, D$_2$O); δ: 1.74–1.95 (1H, m), 2.00 (3H, s), 2.06–2.61 (3H, m), 2.62–3.07 (6H, m), 4.30 (1H, m); MS (FAB, NEG) m/z: 302 (M–H)$^-$ (2) 2-Methylidene-3-oxo-1-cyclopentane carboxylic acid was dissolved in methanol, added 1 equivalent weight of sodium hydroxide and the aqueous solution of sodium salt of N-acetyl-cysteine.

The target compound (IX) was able to be obtained by the same manner of the condensation procedure as that of Example 6 with necessary modification.

(3) Trans-2-(2,3-isopropylidenedioxypropyl) sulfonylmethyl-3-oxo-1-cyclopentane carboxylic acid [Compound (c)] was dissolved in acetone and added 2 equivalent weights of sodium hydroxide. Sodium salt of 2-methylidene-3-oxo-1-cyclopentanecarboxylic acid [the sodium salt of compound (f)] and the sodium (2,3-isopropylidenedioxypropyl)sulfinate was obtained by the reaction of them.

N-acetyl-L-cysteine and 1 equivalent weight of sodium hydroxide were added to the reaction solution to produce the disodium salt of trans-2-[(2-acetylamino-2-carboy-ethyl)-thiomethyl]-3-oxo-1-cyclopentane carboxylic acid [Compound (IX)].

The formation of the sodium salt of 2-methylidene-3-oxo-1-cyclopentane carboxylic acid [Compound (f)] and the sodium (2,3-isopropylidenedioxy)propylsulfinate were confirmed by the chromatography.

Column: Wakosil-II5C 18AR (trademark), diameter 4.6, length 250 mm Developing solvent:Methanol:water:phosphoric acid=75:425:1

Flow rate: 0.8 ml/min

Retention time:

Sodium salt of 2-methylidene-3-oxo-1-cyclopentane carboxylic acid [Compound (f)]: About 12.5 minutes Sodium (2,3-isopropylidene)propylsulfonate: About 10.6 minutes Compound (c): About 14.4 minutes Example 17

Production of 3-acetoxymethyl-2-[(6-methyl-pyrimidin-2-yl)thiomethyl]-cyclopentanone [Compound (XVI)].

3-Acetoxymethyl-2-methylidene-cyclopentanone [compound(b)] (41.5 mg, 0.247 mmol) and 2-mercapto-6-methylpyrimidine(41 mg, 0.247 mmol) were dissolved in methanol(2 ml), acetone (1 ml) and water (1 ml), and stirred at room temperature for 10 hours. Silica gel (250 mg) was added to the reaction solution, and concentrated to dryness. The residue was purified by column chromatography [20 ml, hexane:ethyl acetate=2:1] to obtain the target compound, 3-acetoxymethyl-2-[(6-methylpyrimidin-2-yl)thiomethyl]-cyclopentanone [Compound (XVI)] (13 mg, yield 17.9%).

$^1$H-NMR (200 HMz, CDCl$_3$); δ: 1.58–1.81 (1H, m), 2.03–2.56 (5H, m), 2.05 (3H, s), 2.45 (3H, s), 3.35–3.40 (1H, dd, J=4.43, 14.09 Hz), 3.61–3.74 (1H, dd, J=4.43, 14.09 Hz), 6.84 (1H, d, J=5.13 Hz), 8.35 (1H, d, J=5.13 Hz)

Example 18

Production of (2S,3R)-3-acetoxymethyl-2-[((2RS)-2,3-dihydroxypropyl)thiomethyl]-cyclopentanone [Compound (II')].

A solution of (2S,3R)-2,3-bis(acetoxymethyl)-cyclopentanone [compound (a')][20.56 g, 90.17 mmols] in acetone (178 ml) was added alpha-thioglycerin (9.558 g, 90.17 mmols), and secondly added methanol (20 ml) and aquous 1N-Sodium hydroxide (90.17 ml), and stirred at room temperature for 40 minutes. The reaction solution was adjusted to pH 7.0 by the addition of 1N hydrochloric acid and then concentrated under a reduced pressure to obtain a residue. This residue was dissolved in methanol (200 ml). Silica gel (120 g) added thereto. The solution were concentrated to dryness. The residue was purified by silica gel column chromatography (330 ml, dichloromethane:methanol=25:1–5:1) to obtain the target compound (22.06 g, yield 88.6%).

$^1$H-NMR (200 MHz, CD$_3$OD); δ: 1.56–1.79 (1H, m), 2.07 (3H, s), 2.07 (3H, s), 2.10–2.16 (9H, m), 3.50–3.60 (2H, m), 3.66–3.78 (1H, m), 4.21–4.34 (2H, m); MS (FAB, POS) m/z: 277 (M+H)$^+$

Example 19

Production of (2S,3R)-3-acetoxymethyl-2-[(2RS)-(2,3-isopropylidenedioxypropyl)thiomethyl]-cyclopentanone [Compound (a-1')].

(2S,3R)-3-acetoxymethyl-2-[((2RS)-2,3-dihydroxypropyl)-thiomethyl]-cyclopentanone [compound (II')], (22.06 g, 79.92 mmols) was dissolved in anhydrous acetone (120 ml), added p-toluenesulfonic acid (1.5 g) and dimethoxypropane (29.46 ml, 240 mmols) under ice cooling, stirred at room temperature for 30 minutes. Water (150 ml) and ethyl acetate(300 ml) were added to the reaction solution. The water layer was adjusted to pH 7.0 with a saturated aqueous solution of sodium carbonate and then extracted twice with ethyl acetate (300 ml). The ethyl acetate layer was washed with saturated sodium chloride solution (160 ml), and then dried over anhydrous sodium sulfate, and concentrated under a reduced pressure to obtain the compound (a-1') (24.00 g, yield 95.0%). Without purification, this compound was put to use in the next step.

$^1$H-NMR (200 MHz, CDCl$_3$); δ: 1.35 (3H, s), 1.42 (3H, s), 1.51–1.76 (1H, m), 2.08 (3H, s), 2.10–2.96 (9H, m), 3.65–3.74 (1H, m), 4.05–4.18 (1H, m), 4.18–4.29 (2H, m) MS (FAB, POS) m/z: 317 (M+H)$^+$

Example 20

Production of (2S,3R)-3-hydroxymethyl-2-[((2RS)-2,3-isopropylidenedioxypropyl)thiomethyl]-cyclopentanone (Compound (a-2')].

(2S,3R)-3-acetoxymethyl-2-[((2RS)-2,3-isopropylidene-dioxypropyl) thiomethyl]-cyclopentanone [Compound (a-1')], (25.22 g, 79.81 mmols) was dissolved in methanol (253 ml), added 1N-aqueous solution of sodium hydroxide (50 ml) under ice cooling, stirred at room temperature for 18 minutes. The reaction solution was adjusted to pH 5.8 with 1N hydrochloric acid under ice cooling, and then concentrated under a reduced pressure to obtain a residue. Water (50 ml) was added thereto, and extracted three times with ethyl acetate (200 ml). The ethyl acetate layer was washed with saturated sodium chloride solution (100 ml), dried over anhydrous sodium sulfate, and then concentrated under a reduced pressure to obtain a residue. The residue was purified by silica gel column chromatography (300 ml, dichloromethane:methanol=30:1) to obtain the compound (a-2') {18.67 g, yield 85.3%].

$^1$H-NMR (200 MHz, CDCl$_3$); δ: 1.36 (3H, s), 1.43 (3H, s), 1.58–1.81 (1H, m), 2.00–2.82 (9H, m), 3.02–3.11 (1H, dd, J=3.6 Hz, 13.2 Hz), 3.64–3.73 (1H, m), 3.76–3.91 (2H, m), 4.06–4.34 (2H, m); MS (FAB, POS) m/z: 275 (M+H)$^+$

Example 21

Production of (2S,3R)-3-hydroxymethyl-2-[((2RS)-2,3-isopropylidenedioxypropyl)sulfonylmethyl]- cyclopentanone [Compound (a-3')].

(2S,3R)-3-hydroxymethyl-2-((2RS)-2,3-isopropylidene-dioxypropyl)-thiomethyl]-cyclopentanone [Compound (a-2')][5.558 g, 20.28 mmols] was dissolved in dichloromethane (55 ml), added m-chloro-perbenzoic acid (80% in purity, 8.74g, 40.56mmols) in dichloromethane (85 ml) under ice cooling, and then stirred at room temperature for one hour. The reaction solution was filtered. The filtrate was added 20% aqueous sodium hydrogen sulfite solution (6.48 ml), a saturated aqueous solution of sodium carbonate (16.2 ml), and further water (50 ml), and was stirred for 10 minutes. The mixed solution was separated. The dichloromethane layer was washed with saturated sodium chloride solution (100 ml), dried over anhydrous sodium sulfate, and then concentrated under a reduced pressure to obtain a residue. This residue was purified by silica gel column chromatography (150 ml, hexane : ethyl acetate 1:3) to obtain the compound (a-3') (5.798 g, yield 93.4%).

$^1$H-NMR (200 MHz, CDCl$_3$); δ: 1.38 (3H, s), 1.45 (3H, s), 1.68–1.92 (1H, m), 1.99–2.76 (6H, m), 3.10–3.50 (3H, m), 3.70–4.08 (4H, m), 4.10–4.24 (1H, dd, J=6.14 Hz, 7.42 Hz), 4.56–4.68 (1H, m); MS (FAB, POS) m/z: 307 (M+H)$^+$

Example 22

Production of (1R,2S)-2-[((2RS)-2,3-isopropylidene-dioxypropyl)sulfonylmethyl]-3-oxo-1- cyclopentane carboxylic acid [Compound (c')].

(2S, 3R)-3-hydroxymethyl-2-[((2RS)-(2,3-isopropylidene-dioxypropyl)sulfonylmethyl]-cyclopentanone [Compound (a-3')][5.80 g, 18.94 mmols] was dissolved in acetone (320 ml), added Jones reagent until the color of the reaction solution turned orange color, and stirred. 2-Propanol was added to the mixture until the color of the reaction solution turned green. Then, the reaction solution was concentrated under a reduced pressure to remove acetone. The residue was added water (120 ml) and then extracted twice with dichloromethane (200 ml). The dichloromethane layer was washed with saturated sodium chloride solution (80 ml), dried over anhydrous sodium sulfate, and then concentrated under a reduced pressure to obtain the compound [compound (c'), 4.59 g, yield 75.7%]. Without purification, this compound was put to use in the next step.

$^1$H-NMR (200 MHz, CDCl$_3$); δ: 1.37 (3H, s), 1.43 (1.5H, s), 1.47 (1.5H, s), 2.02 (1H, m), 2.22–2.65 (3H, m), 2.94–3.32 (3H, m), 3.32–3.84 (4H, m), 4.19 (1H, m), 4.40 (1H, brs), 4.59 (1H, m); MS (ESI, NEG) m/z: 319 (M–H)$^-$ Example 23

Production of disodium salt of (1R,2S)-2-[((2R)-2-acetylamino-2-carboxy-ethyl)thiomethyl]-3-oxo-1-yclopentane carboxylic acid [compound (IX'), (cystacyclin)].

A solution of (1R,2S)-2-[((2RS)-2,3-isopropylidenedioxy-propyl)sulfonylmethyl]-3-oxo-1-cyclopentane carboxylic acid [Compound (c')][4.49 g, 14.04 mmols] in acetone (168 ml) was added a solution of N-acetyl-L-cysteine (2.28 g, 14.04 m.mols) in an aqueous 1N sodium hydroxide solution (42.1 ml) and water (15 ml), stirred at room temperature for two hours. The reaction solution was concentrated under a reduced pressure and then the residue purified with Sephadex LH-20 (2.3 L, 80% aqueous methanol) to obtain the disodium salt of compound (IX') (3.72 g, yield 82.2%).

$^1$H-NMR (Compound (IX') sodium salt, 200 MHz, D$_2$O); δ: 1.75–1.93 (1H, m), 1.98 (3H, s), 2.08–2.57 (3H, m) 2.62–2.92 (5H, m), 2.97 (1H, dd, J=4.4, 13.6 Hz), 4.30 (1H, dd, J=4.5, 7.8 Hz); $^{13}$C-NMR (50 MHz, D$_2$O); δ ppm: 226.9, 185.2, 179.9, 176.6, 57.5, 56.0, 52.6, 40.8, 37.9, 33.6, 28.0, 24.8; Ms (fab, pos) m/z: 348 (M+H)$^+$

We claim:

1. A pharmaceutical composition comprising a 2,3-disubstituted cyclopentanone derivative represented by the following general formula (I)

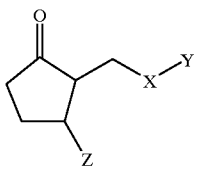

wherein X is S, SO, SO$_2$;
  Y is a hydrocarbon residue having 1–6 carbon atoms, which is substituted or unsubstituted, and having the whole molecular weight of from 15–400 in the residue, and which may contain 1 or 2 hetero atoms in the ring when the residue is a cyclic group and said hetero atom is oxygen, nitrogen or sulfur; and
  Z is a carboxyl group, a group derived therefrom or an aliphatic hydrocarbon residue having 1 to 4 carbon atoms which is substituted or unsubstituted,
    or a pharmacologically acceptable salt thereof,
    except for (1R, 2S)-2-{(2R)-(2-acetylamino-2-carboxy)ethylthio}methyl-3-oxo-1-cyclopentanecarboxylic acid (cystacyclin), and a pharmaceutically acceptable carrier.

2. The pharmaceutical composition of claim 1, wherein the composition is an accelerator of differentiation of neurons.

3. The pharmaceutical composition of claim 1 or 2, wherein Y in the general formula (I) is an alkyl group containing 1–6 carbon atoms and having at least one substituent selected from the group consisting of
  (i) carboxyl group or a group derived therefrom,
  (ii) amino group or a group derived therefrom, and
  (iii) hydroxy group or a group derived therefrom, or pyridino group or pyrimidinyl group which may have one or more substituents.

4. The pharmaceutical composition of claim 3, wherein the substituent on the alkyl group having 1–6 carbon atoms of Y in the general formula (I) is
  (i) carboxyl group or a group derived therefrom, shown as —COR$_1$; R$_1$ is —OR$_2$ or —NR$_3$R$_4$; R$_2$ is a hydrogen atom or hydrocarbon residue having 1–6 carbon atoms; R$_3$ and R$_4$ are hydrogen atoms, an alkyl group having 1–6 carbon atoms or an acyl group having 1–20 carbon atoms respectively,
  (ii) amino group or a group derived therefrom, shown as —NR$_5$R$_6$; R$_5$ and R$_6$ are hydrogen atoms, alkyl group having 1–6 carbon atoms or an acyl group having 1–20 carbon atoms respectively, or
  (iii) hydroxy group or a group derived therefrom, shown as —OR$_7$; R$_7$ is a hydrogen atom, a hydrocarbon residue having 1–6 carbon atoms or an acyl group having 1–20 carbon atoms; and
  carboxyl group or a group derived therefrom in Z of the general formula (I) is the group shown as —COR$_8$ or —CH$_2$OR$_9$; and R$_8$ is independently same as R$_1$; R$_9$ is a hydrogen atom, an alkyl group having 1–6 carbon atoms or an acyl group having 1–20 carbon atoms.

5. The pharmaceutical composition of any one of claims 1 or 2, wherein Z in the general formula (I) is carboxyl group, an alkoxycarbonyl group having 1–6 carbon atoms, hydroxymethyl group or an acyloxymethyl group having 1–20 carbon atoms.

6. The pharmaceutical composition of any one of claims 1 or 2, wherein X in the general formula (I) is S or SO$_2$; Y in the general formula (I) is 2-carboxy-2-aminoethyl group, 2-carboxy-2-(C1–C20)acylaminoethyl group, 2-(C1–C6)alkoxycarbonyl or (C2–C6)alkenyloxycarbonyl-2-aminoethyl group, 2-(C1–C6)alkoxycarbonyl or (C2–C6)alkenyloxyalkoxycarbonyl-2-(C1–C20)acylaminoethyl group, 2,3-dihydroxypropyl group, 2-hydroxyethyl group, 2-aminoethyl group or (C1–C20)acylaminoethyl group; and
  Z in the general formula (I) is hydroxymethyl group or acyloxymethyl group of 1–20 carbon atoms.

7. The pharmaceutical composition of any one of claims 1 or 2, wherein the compound shown as the general formula (I) is:
  (I) the group shown as —CH$_2$—X—Y is —CH$_2$—S—CH$_2$—CH(OH)—CH$_2$OH and Z is —CH$_2$OCOCH$_3$,
  (II) the group shown as —CH$_2$—X—Y is —CH$_2$—S—CH$_2$—CH(COOH)NHCOCH$_3$ and Z is —CH$_2$OCOCH$_3$,
  (III) the group shown as —CH$_2$—X—Y is —CH$_2$—S—CH$_2$—CH(COOH)NHCOCH$_3$ and Z is —CH$_2$OH,
  (IV) the group shown as —CH$_2$—X—Y is —CH$_2$—S—CH$_2$—CH$_2$NHCOCH$_3$ and Z is —CH$_2$OCOCH$_3$,
  (V) the group shown as —CH$_2$—X—Y is —CH$_2$—S—CH$_2$—CH$_2$OH and Z is —CH$_2$OCOCH$_3$,
  (VI) the group shown as —CH$_2$—X—Y is —CH$_2$—S—{3-(COOCH$_3$)-pyridino-2-yl} and Z is —CH$_2$OH,
  (VII) the group shown as —CH$_2$—X—Y is —CH$_2$—S—CH$_2$—CH(COOCH$_3$)NHCOCH$_3$ and Z is —COOH,
  (VIII) the group shown as —CH$_2$—X—Y is —CH$_2$—S—CH$_2$—CH(COOCH$_2$—CH=CH$_2$)NHCOCH$_3$ and Z is —COOH,
  (IX) the group shown as —CH$_2$—X—Y is —CH$_2$—S—CH$_2$—CH(COOH)NHCOCH$_3$ and Z is —COOH (excepting cystacyclin),
  (X) the group shown as —CH$_2$—X—Y is —CH$_2$—S—CH$_2$—CH(COOH)NHCOCH$_3$ and Z is —COOCH$_3$,
  (XI) the group shown as —CH$_2$—X—Y is —CH$_2$—S—CH$_2$—CH$_2$—NHCOCH$_3$ and Z is —COOCH$_3$, or
  (XII) the group shown as —CH$_2$—X—Y is —CH$_2$—S—CH$_2$—CH$_2$—NHCOCH$_3$ and Z is —COOH.

8. The pharmaceutical composition of claim 3, wherein Z in the general formula (I) is carboxyl group, an alkoxycarbonyl group having 1–6 carbon atoms, hydroxymethyl group or an acyloxymethyl group having 1–20 carbon atoms.

9. The pharmaceutical composition of claim 4, wherein Z in the general formula (I) is carboxyl group, an alkoxycarbonyl group having 1–6 carbon atoms, hydroxymethyl group or an acyloxymethyl group having 1–20 carbon atoms.

10. The pharmaceutical composition of claim 3, wherein X in the general formula (I) is S or SO$_2$; Y in the general formula (I) is 2-carboxy-2-aminoethyl group, 2-carboxy-2-(C1–C20)acylaminoethyl group, 2-(C1–C6)alkoxycarbonyl or (C2–C6)alkenyloxycarbonyl-2-aminoethyl group, 2-(C1–C6)alkoxycarbonyl or (C2–C6)alkenyloxyalkoxycarbonyl-2-(C1–C20)acylaminoethyl group, 2,3-dihydroxypropyl group, 2-hydroxyethyl group, 2-aminoethyl group or (C1–C20)acylaminoethyl group; and
  Z in the general formula (I) is hydroxymethyl group or acyloxymethyl group of 1–20 carbon atoms.

11. The pharmaceutical composition of claim 4, wherein X in the general formula (I) is S or SO$_2$; Y in the general formula (I) is 2-carboxy-2-aminoethyl group, 2-carboxy-2-(C1–C20)acylaminoethyl group, 2-(C1–C6)alkoxycarbonyl or (C2–C6)alkenyloxycarbonyl-2-aminoethyl group, 2-(C1–C6)alkoxycarbonyl or (C2–C6)alkenyloxyalkoxycarbonyl-2-(C1–C20)acylaminoethyl group, 2,3-dihydroxypropyl group, 2-hydroxyethyl group, 2-aminoethyl group or (C1–C20)acylaminoethyl group; and Z in the general formula (I) is hydroxymethyl group or acyloxymethyl group of 1–20 carbon atoms.

12. The pharmaceutical composition of claim 8, wherein X in the general formula (I) is S or $SO_2$; Y in the general formula (I) is 2-carboxy-2-aminoethyl group, 2-carboxy-2-(C1–C20)acylaminoethyl group, 2-(C1–C6)alkoxycarbonyl or (C2–C6)alkenyloxycarbonyl-2-aminoethyl group, 2-(C1–C6)alkoxycarbonyl or (C2–C6)alkenyloxyalkoxycarbonyl-2-(C1–C20)acylaminoethyl group, 2,3-dihydroxypropyl group, 2-hydroxyethyl group, 2-aminoethyl group or (C1–C20)acylaminoethyl group; and Z in the general formula (I) is hydroxymethyl group or acyloxymethyl group of 1–20 carbon atoms.

13. The pharmaceutical composition of claim 9, wherein X in the general formula (I) is S or $SO_2$; Y in the general formula (I) is 2-carboxy-2-aminoethyl group, 2-carboxy-2-(C1–C20)acylaminoethyl group, 2-(C1–C6)alkoxycarbonyl or (C2–C6)alkenyloxycarbonyl-2-aminoethyl group, 2-(C1–C6)alkoxycarbonyl or (C2–C6)alkenyloxyalkoxycarbonyl-2-(C1–C20)acylaminoethyl group, 2,3-dihydroxypropyl group, 2-hydroxyethyl group, 2-aminoethyl group or (C1–C20)acylaminoethyl group; and Z in the general formula (I) is hydroxymethyl group or acyloxymethyl group of 1–20 carbon atoms.

14. The pharmaceutical composition of claim 3, wherein the compound shown as the general formula (I) is:

(I) the group shown as —$CH_2$—X—Y is —$CH_2$—S—$CH_2$—CH(OH)—$CH_2$OH and Z is —$CH_2OCOCH_3$, (II) the group shown as —$CH_2$—X—Y is —$CH_2$—S—$CH_2$—CH(COOH)NHCOCH$_3$ and Z is —$CH_2OCOCH_3$, (III) the group shown as —$CH_2$—X—Y is —$CH_2$—S—$CH_2$—CH(COOH)NHCOCH$_3$ and Z is —$CH_2OH$, (IV) the group shown as —$CH_2$—X—Y is —$CH_2$—S—$CH_2$—$CH_2$NHCOCH$_3$ and Z is —$CH_2OCOCH_3$, (V) the group shown as —$CH_2$—X—Y is —$CH_2$—S—$CH_2$—$CH_2$OH and Z is —$CH_2OCOCH_3$, (VI) the group shown as —$CH_2$—X—Y is —$CH_2$—S—{3-(COOCH$_3$)-pyridino-2-yl} and Z is —$CH_2OH$, (VII) the group shown as —$CH_2$—X—Y is —$CH_2$—S—$CH_2$—CH(COOCH$_3$)NHCOCH$_3$ and Z is —COOH, (VIII) the group shown as —$CH_2$—X—Y is —$CH_2$—S—$CH_2$—CH(COOCH$_2$—CH=CH$_2$)NHCOCH$_3$ and Z is —COOH, (IX) the group shown as —$CH_2$—X—Y is —$CH_2$—S—$CH_2$—CH(COOH)NHCOCH$_3$ and Z is —COOH (excepting cystacyclin), (X) the group shown as —$CH_2$—X—Y is —$CH_2$—S—$CH_2$—CH(COOH)NHCOCH$_3$ and Z is —COOCH$_3$, (XI) the group shown as —$CH_2$—X—Y is —$CH_2$—S—$CH_2$—$CH_2$—NHCOCH$_3$ and Z is —COOCH$_3$, or (XII) the group shown as —$CH_2$—X—Y is —$CH_2$—S—$CH_2$—$CH_2$—NHCOCH$_3$ and Z is —COOH.

15. The pharmaceutical composition of claim 4, wherein the compound shown as the general formula (I) is:

(I) the group shown as —$CH_2$—X—Y is —$CH_2$—S—$CH_2$—CH(OH)—$CH_2$OH and Z is —$CH_2OCOCH_3$, (II) the group shown as —$CH_2$—X—Y is —$CH_2$—S—$CH_2$—CH(COOH)NHCOCH$_3$ and Z is —$CH_2OCOCH_3$, (III) the group shown as —$CH_2$—X—Y is —$CH_2$—S—$CH_2$—CH(COOH)NHCOCH$_3$ and Z is —$CH_2OH$, (IV) the group shown as —$CH_2$—X—Y is —$CH_2$—S—$CH_2$—$CH_2$NHCOCH$_3$ and Z is —$CH_2OCOCH_3$, (V) the group shown as —$CH_2$—X—Y is —$CH_2$—S—$CH_2$—$CH_2$OH and Z is —$CH_2OCOCH_3$, (VI) the group shown as —$CH_2$—X—Y is —$CH_2$—S—{3-(COOCH$_3$)-pyridino-2-yl} and Z is —$CH_2OH$, (VII) the group shown as —$CH_2$—X—Y is —$CH_2$—S—$CH_2$—CH(COOCH$_3$)NHCOCH$_3$ and Z is —COOH, (VIII) the group shown as —$CH_2$—X—Y is —$CH_2$—S—$CH_2$—CH(COOCH$_2$—CH=CH$_2$)NHCOCH$_3$ and Z is —COOH, (IX) the group shown as —$CH_2$—X—Y is —$CH_2$—S—$CH_2$—CH(COOH)NHCOCH$_3$ and Z is —COOH (excepting cystacyclin), (X) the group shown as —$CH_2$—X—Y is —$CH_2$—S—$CH_2$—CH(COOH)NHCOCH$_3$ and Z is —COOCH$_3$, (XI) the group shown as —$CH_2$—X—Y is —$CH_2$—S—$CH_2$—$CH_2$—NHCOCH$_3$ and Z is —COOCH$_3$, or (XII) the group shown as —$CH_2$—X—Y is —$CH_2$—S—$CH_2$—$CH_2$—NHCOCH$_3$ and Z is —COOH.

* * * * *